(12) United States Patent
Tremblay

(10) Patent No.: US 8,529,542 B2
(45) Date of Patent: *Sep. 10, 2013

(54) METHOD AND SYSTEM FOR SUSTAINED-RELEASE OF SCLEROSING AGENT

(71) Applicant: UTI Limited Partnership, Calgary (CA)

(72) Inventor: Alain Tremblay, Calgary (CA)

(73) Assignee: UTI Limited Partnership, Calgary (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/675,931

(22) Filed: Nov. 13, 2012

(65) Prior Publication Data

US 2013/0072898 A1   Mar. 21, 2013

Related U.S. Application Data

(63) Continuation of application No. 12/261,652, filed on Oct. 30, 2008, now Pat. No. 8,361,052.

(60) Provisional application No. 60/983,739, filed on Oct. 30, 2007.

(51) Int. Cl.
*A61M 31/00* (2006.01)
*A61B 17/08* (2006.01)

(52) U.S. Cl.
USPC ........... 604/508; 604/500; 604/507; 604/502; 606/214

(58) Field of Classification Search
USPC ................ 604/891.1, 58, 500, 502, 506–508, 604/513; 606/214
See application file for complete search history.

(56) References Cited

U.S. PATENT DOCUMENTS

| 3,960,153 | A | 6/1976 | Carey et al. | 604/164.09 |
| 4,054,139 | A | 10/1977 | Crossley | 604/265 |
| 4,153,058 | A | 5/1979 | Nehme | 604/167.03 |
| 4,185,618 | A | 1/1980 | Corey | 128/831 |
| 5,019,096 | A | 5/1991 | Fox et al. | 600/36 |
| 5,165,953 | A | 11/1992 | Shlenker et al. | 427/2.31 |
| 5,279,551 | A | 1/1994 | James | 604/44 |
| 5,320,110 | A | 6/1994 | Wang | 600/566 |
| 5,395,651 | A | 3/1995 | Sodervall et al. | 427/304 |
| 5,484,401 | A | 1/1996 | Rodriguez et al. | 604/28 |
| 5,709,672 | A | 1/1998 | Illner | 604/265 |

(Continued)

FOREIGN PATENT DOCUMENTS

| CA | 2466636 | 11/2004 |
| CN | 1899629 | 12/2001 |
| WO | WO 2005/007213 | 1/2005 |

OTHER PUBLICATIONS

Bouros et al., "Pleurodesis: everything flows," *Chest*, 118:577-9, 2000.

(Continued)

*Primary Examiner* — Emily Schmidt
*Assistant Examiner* — Bradley G Thomas, Jr.
(74) *Attorney, Agent, or Firm* — Parker Highlander PLLC

(57) ABSTRACT

Methods and systems for treating pleural disease comprising a providing a low dosage of a sclerosing agent over a period of time. Certain examples include catheter with a sclerosing agent that is inserted into the pleural space. The sclerosing agent is released in a sustained-release manner over a period of time to achieve diffuse pleurodesis of the pleural layers.

20 Claims, 14 Drawing Sheets

(56) References Cited

U.S. PATENT DOCUMENTS

| | | | |
|---|---|---|---|
| 6,103,695 A | 8/2000 | Lane et al. | 514/12 |
| 6,530,951 B1 | 3/2003 | Bates et al. | 623/1.45 |
| 6,897,349 B2 | 5/2005 | Gibbins et al. | 602/48 |
| 2002/0010418 A1 | 1/2002 | Lary et al. | 604/101.04 |
| 2002/0133140 A1 | 9/2002 | Moulis | 604/508 |
| 2004/0225254 A1 | 11/2004 | Tanak et al. | 604/58 |
| 2005/0025816 A1 | 2/2005 | Tanaka | 424/445 |
| 2005/0177103 A1 | 8/2005 | Hunter et al. | 604/96.01 |
| 2005/0281822 A1 | 12/2005 | Cedarbaum et al. | 424/145.1 |
| 2005/0281883 A1 | 12/2005 | Daniloff et al. | 424/489 |
| 2006/0009801 A1 | 1/2006 | McGurk et al. | 606/214 |
| 2006/0116721 A1 | 6/2006 | Yun et al. | 607/2 |

OTHER PUBLICATIONS

International Preliminary Report on Patentability issued in PCT/IB2008/003843, dated Mar. 31, 2011.

Marchi et al., "Intrapleural low-dose silver nitrate elicits more pleural inflammation and less systemic inflammation than low-dose talc," *Chest*, 128:1798-1804, 2005.

Office Communication issued in Chinese Patent Application No. 200880122950.4, dated Jun. 5, 2012.

Office Communication issued in New Zealand Patent Application No. 584860, dated Mar. 11, 2011.

Office Communication issued in U.S. Appl. No. 12/261,652, dated Jul. 29, 2010.

Office Communication issued in U.S. Appl. No. 12/261,652, dated Oct. 26, 2010.

Office Communication issued in U.S. Appl. No. 12/261,652, dated Apr. 5, 2011.

Office Communication issued in U.S. Appl. No. 12/261,652, dated Mar. 28, 2012.

Office Communication issued Singapore Patent Application No. 201003075-7, dated Oct. 4, 2011.

Parfrey and Chilvers, "Pleural disease—diagnosis and management," *The Practitioner*, 243:415-21, 1999.

Parulekar et al., "Use of small-bore vs large-bore chest tubes for treatment of malignant pleural effusions," *Chest*, 120:19-25, 2001.

Vargas et al., "Experimental pleurodesis in rabbits induced by silver nitrate or talc: 1-year follow-up," *Chest*, 119:1516-20, 2001.

Vargas et al., "Silver nitrate is superior to talc slurry in producing pleurodesis in rabbits," *Chest*, 118:808-813, 2000.

Bishay et al., "Update of pleural disease-2007," *Annals of Thoracic Medicine*, 2(3):128-142, 2007.

Gaffer et al., "In vitro efficacy of a hydrophilic central venous catheter loaded with silver to prevent microbial colonization," *Zent.bl. Bakteriol.*, 287:157-169, 1998.

Putnam et al., "A randomized comparison of indwelling pleural catheter and doxycycline pleurodesis in the management of malignant pleural effusions," *Cancer*, 86(1): 1992-1999, 1999.

Supplementary European Search Report and issued in Application No. 08848113, dated Mar. 20, 2013.

Individual Specimens – Silver Nitrate Injections

| Number of animals | Concentration AgNO3 | Volume per dose | Total dose (mg/kg) | Daily dose (mg/kg) | Day(s) of administration | Average score (treated) | Average score (control) | Total fluid drained | Max fluid drained in 24 hour period |
|---|---|---|---|---|---|---|---|---|---|
| 2 | 0 % | 1ml/kg | 0 | 0.00 | 1 | 1 | 1 | 0.7 | 0.4 |
| 2 | 0 % | 1ml/kg | 0 | 0.00 | 5 | 1 | 1 | 2.3 | 0.9 |
| 2 | 0.85 % | 1ml/kg | 8.5 | 8.00 | 1 | 8 | 1.5 | 59.25 | 25 |
| 2 | 0.425 % | 1ml/kg | 4.25 | 4.25 | 1 | 8 | 1 | 47 | 21 |
| 2 | 0.085 % | 1ml/kg | 0.8 | 0.80 | 1 | 4.75 | 1 | 48 | 19 |
| 2 | 0.085 % | 1ml/kg | 4.25 | 0.80 | 5 | 7.5 | 1 | 0.5 | 0.5 |
| 2 | 0.085 % | 1ml/kg | 11.9 | 0.80 | 14 | 8 | 1 | 55.5 | 20 |
| 2 | 0.05 % | 1ml/kg | 0.5 | 0.50 | 1 | 1.5 | 1 | 0.25 | 0.5 |
| 4 | 0.05 % | 1ml/kg | 2.5 | 0.50 | 5 | 3.25 | 1 | 16.75 | 5 |
| 4 | 0.05 % | 1ml/kg | 7 | 0.50 | 14 | 6.5 | 1 | 21 | 4.625 |

FIG. 3A

Average pleurodesis score on treated side with multi-day silver nitrate injections

| Days\Concentration SN | 0.850% | 0.425% | 0.085% | 0.050% | Placebo |
|---|---|---|---|---|---|
| 1 | 8 | 8 | 4.75 | 1.5 | 1 |
| 5 | | | 7.5 | 3.25 | 1 |
| 14 | | | 8 | 6.5 | 1.5 |

FIG. 3B

Average Pleurodesis Score on Treated Side with Multi-Day Silver Nitrate Injections

| N | Volume per dose | Total dose (mg/kg) | Daily dose (mg/kg) | Day(s) of administration | Average score (treated) | Average score (control) | Total fluid drained | Max fluid drained in 24 hour period |
|---|---|---|---|---|---|---|---|---|
| 2 | 1ml/kg | 0 | 0.00 | 1 | 1 | 1 | 0.7 | 0.4 |
| 2 | 1ml/kg | 0 | 0.00 | 5 | 1 | 1 | 2.3 | 0.9 |
| 2 | 1ml/kg | 10 | 10.00 | 1 | 4.5 | 1 | 8 | 6 |
| 2 | 1ml/kg | 5 | 5.00 | 1 | 2.5 | 1 | 22.5 | 9 |
| 2 | 1ml/kg | 25 | 5.00 | 5 | 5 | 1 | 5.5 | 5.5 |
| 2 | 1ml/kg | 70 | 5.00 | 14 | 7.5 | 1 | 20 | 7 |
| 2 | 1ml/kg | 5 | 1.00 | 5 | 1 | 1 | 0 | 0 |
| 2 | 1ml/kg | 14 | 1.00 | 14 | 1 | 1 | 0 | 0 |

| Average Pleurodesis Score on Treated Side with Multi-Day Injections of Deoxycycline |||||
|---|---|---|---|---|
| Days/Doxycycline(mg/kg) | 10 mg/kg | 5 mg/kg | 1 mg/kg | Placebo |
| 1 | 4.5 | 2.50 | | 1 |
| 5 | | 5.00 | 1 | 1 |
| 14 | | 7.50 | 1 | 1.5 |

Scale for macroscopic pleural evaluation.

A score of ≥5 is considered a successful pleurodesis.

| 1 | No adhesions between the visceral and parietal pleura. |
|---|---|
| 2 | Rare adhesions between the visceral and parietal pleura with no symphysis. |
| 3 | A few scattered adhesions between the visceral and parietal pleura with no symphysis. |
| 4 | Many diffuse adhesions between the visceral and parietal pleura away from catheter site with no symphysis. |
| 5 | Many diffuse adhesions between the visceral and parietal pleura away from catheter site with symphysis involving less than 5% of the hemithorax or limited to catheter site. |
| 6 | Many diffuse adhesions between the visceral and parietal pleura away from catheter site with symphysis involving 5 to 25% of the hemithorax and with a component of symphysis away from the catheter site. |
| 7 | Many diffuse adhesions between the visceral and parietal pleura away from catheter site with symphysis involving 25 to 50% of the hemithorax and with a component of symphysis away from the catheter site. |
| 8 | Many diffuse adhesions between the visceral and parietal pleura away from catheter site with symphysis involving greater than 50% of the hemithorax and with a component of symphysis away from the catheter site. |

FIG. 5

Mean Scores

| Catheter Type | Dose | Score treated side | Score control side |
|---|---|---|---|
| Uncoated | 0 mg | 1 | 1 |
| Silver Nitrate | 24 mg | 4.82† | 1‡ |
| Silver Nitrate | 50 mg | 7.4† | 1.6* |

†p=0.001 vs uncoated
*p=0.011 vs contralateral side
‡p=0.005 vs contralateral side Pleurodesis Scores for Large Animals treated with Silver Nitrate Sustained Release Catheters

| Dose: | 1 g | | 750mg | | Placebo | |
|---|---|---|---|---|---|---|
| | Score Treated Side | Score Untreated Side | Score Treated Side | Score Untreated Side | Score Treated Side | Score Untreated Side |
| | 8 | 1 | 5 | 1 | 1 | 1 |
| | 7 | 1 | 8 | 1 | 1 | 1 |
| | 7 | 1 | 7 | 1 | 1 | 1 |
| | * | 1 | ** | ** | 1 | 1 |
| Average | 7.33 | 1.00 | 6.67 | 1.00 | 1.00 | 1.00 |

*removed day 3. **did not undergo catheter placement

METHOD AND SYSTEM FOR SUSTAINED-RELEASE OF SCLEROSING AGENT

RELATED APPLICATIONS

The present application is a continuation of co-pending U.S. patent application Ser. No. 12/261,652 filed Oct. 30, 2008 which claims priority to U.S. Provisional Patent Application No. 60/983,739 filed Oct. 30, 2007, the entire contents of which are herein incorporated by reference.

FIELD OF THE INVENTION

The present disclosure relates generally to a method and system for treating pleural diseases. More particularly, the present disclosure relates to a method and system for treating pleural diseases comprising providing a low dosage of a sclerosing agent over a period of time to achieve diffuse pleurodesis of the pleural layers. Still more particularly, the present disclosure relates to a catheter coated with a sclerosing agent that provides drainage and achieves pleurodesis of the pleural layers via sustained-release of the sclerosing agent.

BACKGROUND INFORMATION

Pleural diseases are frequent medical problems often requiring expensive inpatient treatments, often of an invasive or surgical nature. Non-limiting examples of pleural diseases include pleural effusions and pneumothorax. Pleural effusions are build-ups of fluid around the lung, and pneumothorax (PTX) is the collapse of the lung due to air entering the pleural space.

Pleural effusions can be caused by a variety of common medical conditions such as cancer, tuberculosis, congestive heart failure, pneumonia, pulmonary emboli, cirrhosis with ascites, pancreatitis, or collagen vascular disease. If the amount of fluid is significant, the lung is compressed and the patient experiences shortness of breath and cough. These effusions are often difficult to treat and result in recurrent shortness of breath as well as frequent hospital visits for multiple treatments. There are many different elements that should be taken into consideration for the treatment and management of pleural effusions, particularly malignant pleural effusions. See American Thoracic Society, *Management of Malignant Pleural Effusions,* 162 AM. J. OF RESPIRATORY AND CRITICAL CARE 1987-2001 (2000, incorporated herein by reference).

In view of the burden and suffering attributable to pleural effusions and of the nature of the patient population suffering from it, a preferred treatment approach should offer immediate and long term relief of symptoms, avoid hospitalization, be applicable to the majority of patients, have minimal side effects and avoid repeated uncomfortable procedures.

The usual approach to patients with symptomatic malignant pleural effusion (MPE) is to perform repeated pleural taps (thoracentesis), or to attempt pleurodesis with a sclerosing agent such as talc or a tetracycline by placing an intercostal catheter or via surgical thoracoscopy and attempt pleurodesis with a sclerosing agent such as talc or a tetracycline. The first approach is resource intensive (requiring multiple visits to physician or ultrasound department), painful and only partially and temporarily effective in relieving symptoms. The second requires hospitalization, and may require a general anesthetic. It can also only be performed in a portion of patient who undergo chest tube placement, can be significantly painful and has been associated with severe pulmonary complications.

A newer outpatient procedure, the Pleurx, has been developed by Denver Biomed, Inc. (now part of Cardinal Health) using a long-term tunneled catheter inserted into the pleural space. Unfortunately, the majority of patients need ongoing drainage with the catheter for the rest of their life, although some patients achieve a pleurodesis after an average of approximately 8-12 weeks of drainage. This prolonged drainage has potential impacts on quality of life, complication rates (due to infections), cost of supplies and nutritional status.

Primary spontaneous pneumothorax (PSP) is a pneumothorax in patients without a pre-existing lung disease. Secondary spontaneous pneumothorax (SSP) is a pneumothorax occurring in patients with a variety of lung diseases such as chronic obstructive pulmonary disease (COPD), emphysema, or pulmonary fibrosis. The majority of pneumothorax cases can be treated with simple chest tube drainage. Although patients who experience a pneumothorax are at high risk of a recurrent event in the future, patients are not generally offered treatment aimed to reduce that risk until they experience two or more episodes of lung collapse given the invasive nature of currently available preventative treatments.

Patients with severe heart failure can develop recurrent pleural effusions complicating their care and causing increased breathing difficulties. Given the lack of effective and safe local treatments for these effusions, only optimization of the cardiac function can lead to the resolution of the problem. Unfortunately, recurrence of the fluid build up is frequent.

A safe, minimally invasive and effective method to achieve long term control of pneumothorax or non-malignant pleural effusions would be of great benefit to these patients.

SUMMARY

A method and system of providing treatment for pleural diseases, while minimizing the associated problems of existing treatment options, is desired. Embodiments of the present disclosure comprise a method and system for treating pleural diseases by providing a low dosage of a sclerosing agent over a period of time to achieve pleurodesis of the pleural layers. Specific exemplary embodiments comprise a catheter coated with a sclerosing agent that achieves pleurodesis of the pleural layers via sustained-release of the sclerosing agent. By providing the sclerosing agent over a period of time, rather than as a large single dose, the negative side effects (such as patient discomfort) should be reduced. The use of a catheter with a sustained-release sclerosing agent can also offer immediate and long term relief of symptoms, avoid hospitalization, be applicable to a majority of patients, have minimal side effects and avoid repeated uncomfortable procedures.

Exemplary embodiments of the present disclosure comprise methods and systems for treating pleural disease, including pleural effusions. Exemplary embodiments comprise providing a low dosage level of a sclerosing agent over a period of time to achieve pleurodesis of the pleural layers, which can reduce the likelihood that pneumothorax or pleural effusions will re-form. The dosage level can be selected at a level that is low enough to minimize or reduce negative side effects generally associated with administering a sclerosing agent in a single dose to achieve pleurodesis. The dosage level can be selected at a level that is below the minimum amount believed to be therapeutically effective in a single dose. However, pleurodesis can still be achieved because of the repeated (or sustained-release) dosing.

Certain examples include a catheter with a sclerosing agent that is inserted into the pleural space. The sclerosing agent can be released in a sustained-release manner over a period of time to achieve a general or diffuse pleurodesis of the pleural layers. In certain embodiments, the majority of the sclerosing agent (e.g. greater than fifty percent of the total amount of sclerosing agent contained on or in the catheter) can be released at a steady-state rate over twelve, twenty-four, thirty-six, forty-eight, sixty, or seventy-two hours. In certain embodiments, the majority of the sclerosing agent can be released over a period ranging from three to fifteen days. In specific embodiments, the sclerosing agent may be released so that approximately ten percent of the sclerosing agent is released every two, four, six, eight, ten, twelve, fourteen, sixteen, eighteen, twenty, twenty-two, twenty-four, twenty-six, twenty-eight, thirty, thirty-two, thirty-four, or thirty-six hours. In addition, the catheter can be used to drain fluid or air from the pleural space. In certain examples, a suction and/or storage device can be coupled to the catheter to assist in removing and storing the fluid or air. In specific examples, the sclerosing agent is silver nitrate.

By administering the sclerosing agent in a sustained-release manner with a single procedure, the patient can avoid multiple treatment procedures and avoid long hospitalization requirements.

Certain embodiments comprise a method of promoting pleurodesis. The method may comprise providing a catheter comprising a proximal end, a distal end, and a sclerosing agent proximal to the distal end. The sclerosing agent may be configured to promote inflammation or fibrosis of a pleural layer. The method may include inserting the distal end of the catheter into a pleural space between a first pleural layer and a second pleural layer, providing a sustained-release of the sclerosing agent over a period of time into the pleural space, and creating a diffuse pleurodesis of the first and second pleural layers. In certain embodiments, the period of time may be greater than or equal to twenty-four hours. In other embodiments, the period of time may be greater than twelve, forty-eight or seventy-two hours. In still other embodiments, the time period may be between three and fifteen days. In specific embodiments, the sclerosing agent comprises silver nitrate.

In certain embodiments, the first pleural layer is a visceral pleural layer and the second pleural layer is a parietal pleural layer. In specific embodiments, the diffuse pleurodesis comprises a pleurodesis of at least twenty-five percent of a hemithorax, and the visceral pleural layer is fused to the parietal pleural layer in a plurality of locations. In other embodiments, the diffuse pleurodesis comprises a pleurodesis of at least fifty percent of a hemithorax, and the visceral pleural layer is fused to the parietal pleural layer in a plurality of locations.

In certain embodiments, the diffuse pleurodesis comprises multiple adhesions between the first pleural layer and the second pleural layer, and a portion of the multiple adhesions may be located at least three centimeters from the distal end of the catheter when the distal end is inserted into the pleural space. Specific embodiments may also comprise draining a pleural effusion or air from the pleural space via the catheter.

In specific embodiments, the pleural effusion may be associated with cancer, congestive heart failure, cirrhosis, tuberculosis, pneumonia, pulmonary emboli, pancreatitis, or collagen vascular disease. In certain embodiments, the pleural effusion may comprise a malignant pleural effusion.

Certain embodiments may also comprise providing a device that creates a negative pressure, coupling the device to the catheter, and operating the device provide a negative pressure to the pleural space. Specific embodiments may also comprise draining the pleural effusion into a container coupled to the device.

Specific embodiments comprise a method of treating a pleural disease. The method may comprise providing a catheter comprising a proximal end, a distal end, and a sclerosing agent proximal to the distal end. The sclerosing agent may be configured to promote inflammation or fibrosis of a pleural layer. The method may also comprise inserting the distal end of the catheter into a pleural space between a first pleural layer and a second pleural layer, withdrawing a pleural effusion or air from the pleural space via the catheter, and providing a sustained-release of the sclerosing agent over a period of time into the pleural space. The method may also comprise creating a diffuse pleurodesis of the first pleural layer to the second pleural layer. In specific embodiments, the period of time is greater than or equal to twenty-four hours. In specific embodiments, the time period may be between three and fifteen days. In certain embodiments, the pleural disease is pneumothorax. In specific embodiments, the sclerosing agent comprises silver nitrate. Certain embodiments may also comprise providing a device that creates a negative pressure, coupling the device to the catheter, and operating the device provide a negative pressure to the pleural space.

Specific embodiments may also comprise a method of fusing two pleural layers. In certain embodiments, the method may comprise providing a catheter coated with silver nitrate, wherein the catheter comprises a proximal end and a distal end. The method may also comprise inserting the distal end of the catheter into a pleural space between a first pleural layer and a second pleural layer, where the distal end of the catheter is inserted in an insertion point. The method may also comprise providing a sustained release of the silver nitrate into the pleural layer, and creating a pleurodesis of the first pleural layer and the second pleural layer, where the pleurodesis comprises a plurality of adhesions between the first pleural layer and the second layer. In certain embodiments, the plurality of adhesions cover at least twenty-five percent of the surface area of the first pleural layer, and at least one of the adhesions is more than five centimeters from the insertion point. In certain embodiments, the sustained release of silver nitrate into the pleural layer occurs over a time period of at least twelve hours.

Certain embodiments comprise a method of coating a catheter comprising: (a) introducing a catheter or a portion thereof to be coated into a chitosan solution and optionally holding the catheter or portion thereof in this solution for a first time period, wherein the chitosan solution comprises acetic acid; followed by (b) introducing the catheter or the portion thereof into a first silver nitrate solution and optionally holding the catheter or the portion thereof in this solution for a second time period; followed by (c) introducing the catheter or the portion thereof into a second silver nitrate solution and optionally holding the catheter or the portion thereof in this solution for a third time period. In certain embodiments, the method also comprises (d) drying the catheter or the portion thereof; (e) repeating steps (a)-(c) to form a hydrogel, and either: (i) introducing the catheter or the portion thereof to a glutaraldehyde solution and optionally holding the catheter or the portion in this solution for a fourth time period; or (ii) introducing the catheter or the portion thereof to a sodium hyaluronate solution and optionally holding the catheter or the portion in this solution for a fifth time period, followed by introducing the catheter or the portion thereof to a third silver nitrate solution and optionally holding the catheter or the portion thereof in this solution for a sixth time period. In specific embodiments, following step (i) or (ii), the catheter or the portion thereof is dried.

In certain embodiments, the first time period may be about 5-10 seconds, the second time period may be about 1-2 minutes, the third time period may be about 24 hours, the fourth time period may be about 8 minutes, and/or the sixth time period may be about 4 hours. In certain embodiments, the concentration of chitosan ranges from about 1.4-1.8% (w/w). In specific embodiments the concentration of chitosan may range from about 1.0-2.0% (w/w). In specific embodiments, the molecular weight of the chitosan may range from about 400,000 to 600,000 g/mol. In certain embodiments the molecular weight of the chitosan may range from 150,000-700,000 g/mol. In certain embodiments, the degree of acetylation of the chitosan is about 18-20%. In specific embodiments, the degree of acetylation of the chitosan is about 15-24% (w/w). In specific embodiments, the temperature of the chitosan solution is about 5° C. In certain embodiments, the temperature of the chitosan solution is about 2-8° C. In certain embodiments, the concentration of acetic acid is about 1% (w/w). In specific embodiments, the concentration of acetic acid is about 0.6-1.5%. The acetic acid solution may be prepared using deionized water, double distilled water, or other forms of water without Cl ions. In certain embodiments, the concentration of the first and/or second silver nitrate solution is about 14-18% (w/w). In other embodiments, the concentration of the first and/or second silver nitrate solution is about 10-15% (w/w).

In specific embodiments, the first silver nitrate solution is comprised in a precipitation tube. In certain embodiments, one or more silver nitrate solutions may be prepared using deionized water, double distilled water, or other forms of water without Cl ions. In specific embodiments, the concentrations of the first and second silver nitrate solutions are the same, while in other embodiments, the concentrations of the first and second silver nitrate solutions are different. In certain embodiments, the first time period may be about 1 minute. In specific embodiments, the first time period may be about 1-5 minutes. In specific embodiments, the second time period may be about 5 minutes. In certain embodiments, the second time period may be about 2-9 minutes. In certain embodiments, the third time period may be about 24 hours. In certain embodiments, the third time period may be about 20-40 hours.

In specific embodiments, the period of time between step (b) and step (c) is less than about 5 seconds. In certain embodiments, the period of time between step (b) and step (c) is less than about 2-10 seconds. In certain embodiments, the catheter or the portion thereof is cleaned prior to step (a). In specific embodiments, the cleaning comprises contacting the catheter or the portion thereof with about 98% (w/w) ethanol. In specific embodiments, the cleaning comprises contacting the catheter or the portion thereof with about 70-98% (w/w) ethanol. In certain embodiments, the catheter or the portion thereof is not dried between steps (b) and (c). In specific embodiments, following step (e), the catheter or portion thereof is rinsed in distilled water. In certain embodiments, the catheter or portion thereof is rinsed in distilled water for about 10-20 seconds following step (e).

In specific embodiments, the concentration of glutaraldehyde is about 0.98%. In specific embodiments, the concentration of glutaraldehyde is about 0.7-1.5% (w/w). In certain embodiments, the glutaraldehyde solution is prepared using deionized water, double distilled water, or other forms of water without Cl ions. In certain embodiments, the fourth time period is about 8 minutes. In certain embodiments, the fourth time period is about 6-12 minutes. In specific embodiments, the catheter or the portion thereof is rinsed in distilled water immediately before step (i) and/or immediately before drying. In certain embodiments, the concentration of third silver nitrate solution is about 16%. In certain embodiments, the concentration of third silver nitrate solution is about 14-20%, and/or the concentration of sodium hyaluronate is about 1-3% (w/w). In specific embodiments, the fifth time period is about 3-6 hours, and/or the sixth time period is about 48-62 hours.

In certain embodiments, the drying step of step (f) is performed at 12-37 C temperature. In specific embodiments, the degree of swelling of the hydrogel, $\alpha$, is about 125. In specific embodiments, the degree of swelling of the hydrogel, $\alpha$, is about 125-220%. In certain embodiments, the catheter or portion thereof comprises silicone-, polyurethane, or PVC.

Embodiments may also comprise method of coating a catheter or portion thereof to be coated comprising: (a) forming a first coating on a catheter or the portion thereof, comprising sequentially coating the catheter or the portion thereof with layers in the following order: a first chitosan layer, a first silver nitrate layer and a second silver nitrate layer; (b) forming a second coating on the catheter or the portion thereof that is layered on top of the first coating, comprising sequentially coating the catheter or the portion thereof with layers in the following order: a second chitosan layer, a third silver nitrate layer and a fourth silver nitrate layer; and (c) following step (b), introducing the catheter or the portion thereof to a glutaraldehyde solution; and (d) drying the catheter or the portion thereof.

Embodiments may also comprise a method of coating a catheter or the portion thereof to be coated comprising: (a) forming a first coating on a catheter or the portion thereof, comprising sequentially coating the catheter or the portion thereof with layers in the following order: a first chitosan layer, a first silver nitrate layer and a second silver nitrate layer; (b) forming a second coating on the catheter or the portion thereof that is layered on top of the first coating, comprising, following step (a), sequentially coating the catheter or the portion thereof with layers in the following order: a second chitosan layer, a third silver nitrate layer and a fourth silver nitrate layer; and (c) following step (b), introducing the catheter or the portion thereof to a sodium hyaluronate solution, followed by introducing the catheter or the portion thereof to a fifth silver nitrate solution; and (d) drying the catheter or the portion thereof.

In certain embodiments of any aspect of the present invention, agents other than silver nitrate may be employed. Non-limiting examples of such agents include silver metal, silver oxide, or silver salts, including silver sulfate, silver carbonate, silver phosphate, silver sulfide, silver iodate, silver halides (e.g., silver chloride) and silver sulphadiazine.

It is contemplated that any embodiment discussed in this specification can be implemented with respect to any method or system of the invention, and vice versa. Furthermore, systems of the invention can be used to achieve methods of the invention.

The terms "general pleurodesis" or "diffuse pleurodesis" are defined as pleurodesis that is distributed throughout the pleural layers and not confined to a specific location. General or diffuse pleurodesis comprises adhesion or fusion of the pleural layers that is not limited to the location at which a sclerosing agent is introduced into the pleural space. In certain non-limiting examples, general or diffuse pleurodesis comprises adhesion or fusion of the pleural layers at a distance measured 3 cm, 4 cm, 5 cm, or more from the location in which a sclerosing agent is introduced. In certain non-limiting examples, general of diffuse pleurodesis can also comprise adhesion or fusion of more than twenty percent, thirty percent, forty percent, or fifty percent of the pleural layers. In certain non-limiting examples, general of diffuse pleurodesis can also comprise adhesion or fusion of the pleural layers at multiple locations.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The terms "inhibiting" or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

As used herein, "introducing" and variants thereof refer to placing a catheter, or catheter coated at least one layer as described herein, into physical contact with a solution. Non-limiting methods of such introduction include submerging and dipping.

As used herein, the term "about" is used to indicate that a value includes the standard deviation of error for the device and/or method being employed to determine the value.

Other objects, features, and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

FIGS. 3A-3C illustrate experimental results using direct daily dose injections of silver nitrate FIGS. 4A-4C illustrate experimental results using direct daily dose injections of doxycycline.

FIG. 5 illustrates a table of a standard grading system used to evaluate experimental results.

DETAILED DESCRIPTION OF EXEMPLARY EMBODIMENTS

Figure 1:
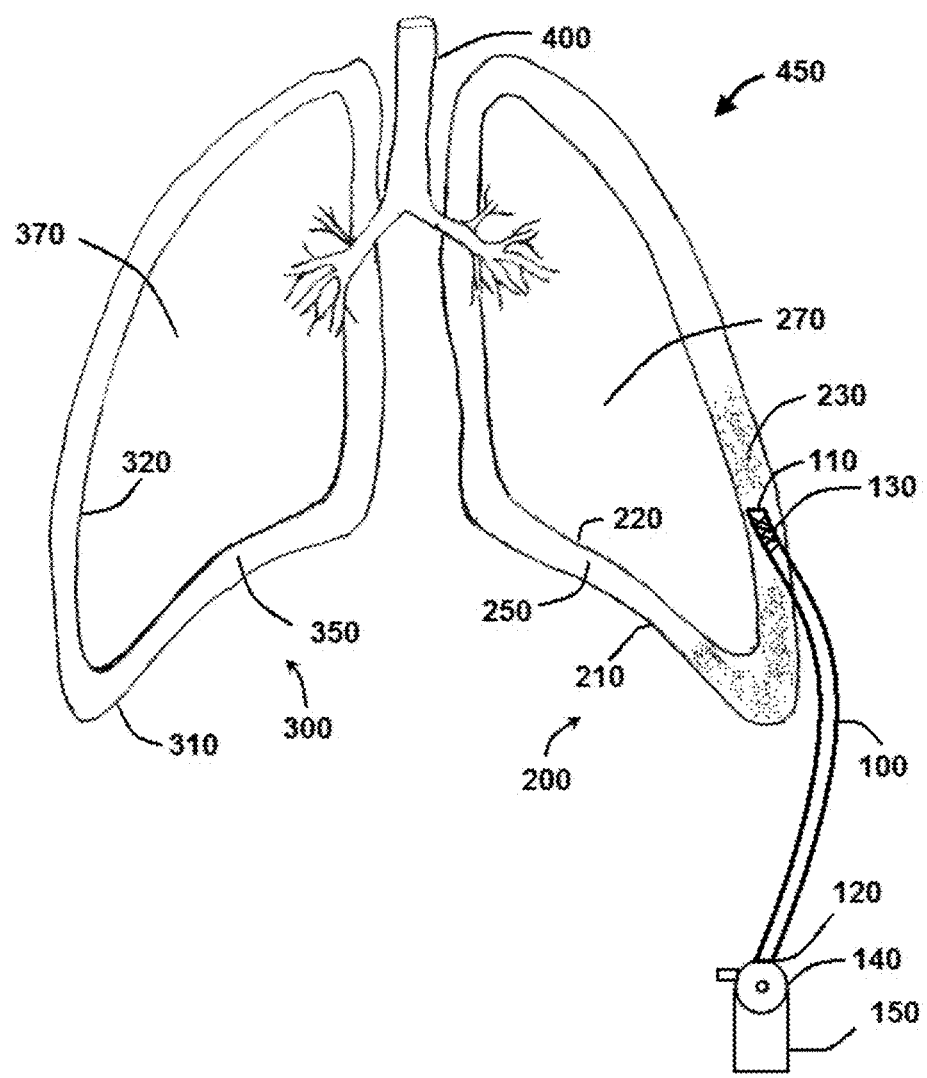
FIG. 1 illustrates a schematic and section view of an exemplary embodiment of a catheter installed in a pleural space.

Referring now to the exemplary embodiment shown in FIG. 1, a thoracic cavity 450 comprises a right hemithorax 200, a left hemithorax 300, and a trachea 400. Right hemithorax 200 comprises a pleural space 250 between a parietal layer 210 and a visceral layer 220, which encompasses a right lung 270. Similarly, left hemithorax 300 comprises a pleural space 350 between a parietal layer 310 and a visceral layer 320, which encompasses a left lung 370. FIG. 1 is not to scale, and certain portions may be enlarged to provide clarity and detail.

Under certain conditions described elsewhere in this disclosure, a pleural effusion 230 or air can accumulate in pleural space 250 between parietal layer 210 and visceral layer 220. In order to drain pleural effusion 230 or air from pleural space 250, a catheter 100 can be inserted into pleural space 250. In the exemplary embodiment shown, catheter 100 comprises proximal end 120, a distal end 110 and a sclerosing agent 130 proximal to distal end 110. In certain embodiments, catheter 100 may be coupled to a negative pressure device 140 and/or a container 150. Negative pressure device 140 can be any small, portable, lightweight device capable of creating a negative pressure in catheter 100 and pleural space 250. In certain embodiments, negative pressure device may be vacuum pump or vacuum compressor. Container 150 is configured to receive and contain fluid/air from pleural effusion 230 as it drains from pleural space 250 through catheter 100.

In the exemplary embodiment shown in FIG. 1, distal end 110 of catheter 100 is inserted into pleural space 250 so that the portion of catheter 100 comprising sclerosing agent 130 is also placed in pleural space 250. In certain embodiments, sclerosing agent 130 comprises a material, such as silver nitrate, that promotes inflammation and/or fibrosis of parietal layer 210 and/or visceral layer 220. By promoting inflammation and/or fibrosis of parietal layer 210 and/or visceral layer, the pleural layers can become fused to achieve general or diffuse pleurodesis. This can help to prevent the re-accumulation of fluid or air in pleural space 250 and thereby reduce the likelihood of pleural effusions/PTX reforming. In other embodiments, sclerosing agent 130 may comprise a different material, or combination of materials, than silver nitrate. A non-limiting list of exemplary materials that sclerosing agent 130 may comprise includes: doxycycline, minocycline, tetracycline, talc, bleomycin, doxorubicin, proviodine, TGF beta, mepacrine, other antibiotics, other antineoplastic agents, and other cytokines and biological agents.

In exemplary embodiments, catheter 100 is configured for sustained-release of sclerosing agent 130 into pleural space 250 over an extended period of time. In certain examples, sclerosing agent 130 may be released over a period of time ranging from twenty-four hours to several days. By allowing sclerosing agent 130 to be released over an extended period of time, it is believed that potential side effects related to the pleurodesis can be minimized. Rather than injecting the sclerosing agent in a single dose, the agent is administered in a sustained manner over a period of time. It is believed that the sclerosing agent can be administered at a level sufficient to achieve the desired pleurodesis, yet low enough to reduce side effects common with single dose administrations. Such side effects include patient discomfort and pulmonary complications. In certain embodiments, catheter 100 can be inserted into pleural space 250 on an out-patient basis. Such a procedure can reduce the cost and inconvenience to the patient for treating pleural effusion 230.

Figure 2:
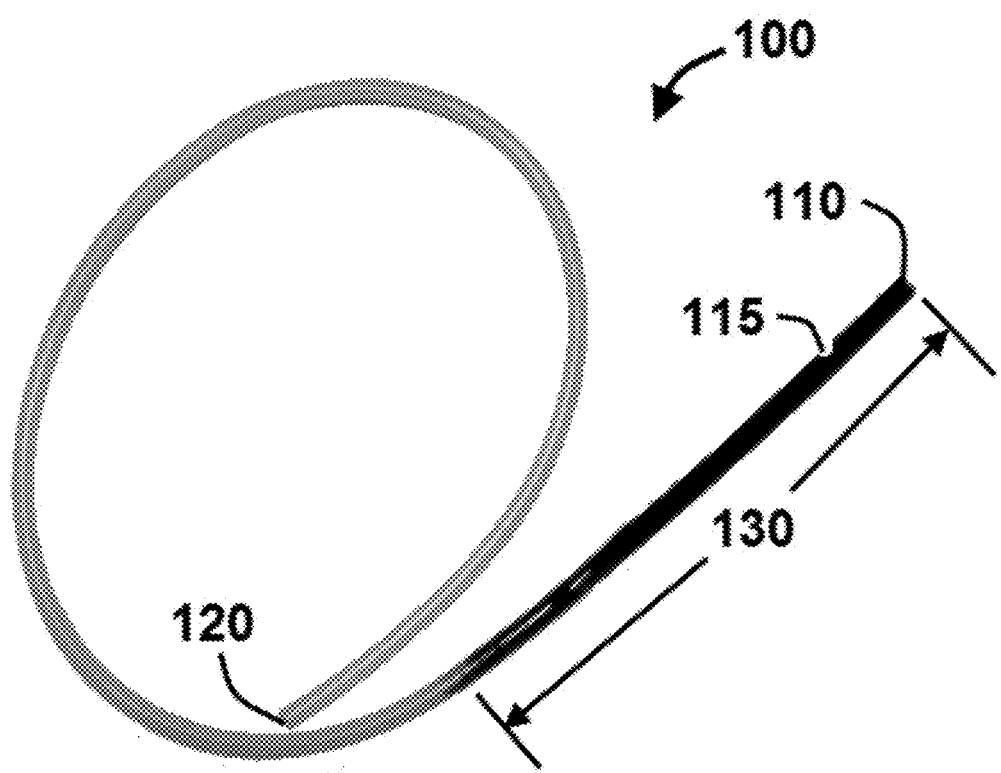
FIG. 2 illustrates an exemplary embodiment of a catheter.

One exemplary embodiment of catheter 100 is shown in FIG. 2. In this embodiment catheter 100 comprises a side drainage hole 115 to facilitate drainage of pleural space 250. Other embodiments may comprise additional side drainage holes. Side drainage hole 115 provides an additional path for fluid or air to flow into catheter 100 in the event that distal end 110 should become blocked.

Sclerosing agent 130 can be applied to catheter 100 by one of many methods, including but not limited to, spin coating, spraying, dipping, surface impregnating, etc. Specific embodiments of coating are described in the section below entitled "Preparation of Coated Catheters".

In certain embodiments, the use of negative pressure device 140 may also assist in achieving pleurodesis of parietal layer 210 and visceral layer 220. Sclerosing agent may also be applied in a method such as that disclosed in U.S. Pat. No. 6,287,285, herein incorporated by reference. Negative pressure device 140 can assist in providing apposition of parietal layer 210 and visceral layer 220, which can reduce the likelihood of fluid/air accumulation between the layers and allow for sclerosing agent 130 to effectively fuse the layers. In certain embodiments, negative pressure device 140 provides a negative pressure of approximately 5-40 centimeters of water. Negative pressure device 140 may also comprises a backflow device (such as a check valve, not shown) to prevent fluid or air from returning through catheter 100 to pleural space 250.

Container 150 can be coupled to negative pressure device 140 to capture accumulation of fluid/air removed from pleural space 250. In certain embodiments, container 150 has a capacity of approximately 500 milliliters, and is removably secured to negative pressure device 140. In certain embodiments, container 150 can easily removed from catheter 100 and/or negative pressure device so that container 150 can be emptied of fluid drained from pleural space 250. In certain embodiments, a container may be coupled to the catheter without a negative pressure device.

While an exemplary embodiment is described herein, it will be understood that various modifications to the method and system can be made without departing from the scope of the present invention. For example, the composition of the sclerosing agent may be different in other embodiments. Furthermore, the sequential recitation of steps in any claim is not a requirement that the steps be performed in any particular order, unless otherwise so stated.

Preparation of Coated Catheters

Metallic ions (e.g., gold, silver, copper) have a broad spectrum antimicrobial activity (Spadaro et al., 1974; Schaeffer et al., 1988). Silver ions are used for prevention of bacterial colonization on catheters (Maki et al., 1988; Groeger et al., 1993; Raad et al., 1996). The silver ions are deposited on the catheter as a fine coat of metallic silver, typically with a thickness of ≦1 μm, by a process which utilizes low temperature vapor and a large vacuum (Sioshansi, 1991; Sioshansi, 1994; Sioshansi and Tobin, 1995; Bambauer et al., 1998). This technology has been applied to catheters made of silicone, polyurethane and other polymers. Currently, catheters with silver coatings are used in combination with antimicrobial agents such as benzalkonium chloride (BKC) (Li et al., 1999) which has been deposited on catheters made of polyurethane (Maki et al., 1997; Hentschel and Munstedt, 1999) and silicone (Raad et al., 1996). Methods used to deposit silver ions on the surface of catheters can be classified as follows: (i) inclusion of silver nanoparticles (Samuuel and Guggenbichler, 2004), and (ii) silver coated in a steam phase (Tobin and Bambauer, 2003). Vargas et al./16/showed that silver nitrate administered in the pleural space is an effective way of producing pleurodesis, and silver nitrate is a known sclerosing agent (Bouros et al., 2000; Gallivan, 2001).

The present invention regards silver nitrate hydrogels that have been coated on the surface of polyurethane and silicone catheters. To create the coating, two different methods were employed: a chelation reaction between chitosan and silver ions, followed by (i) chelation reaction between chitosan and silver ion and finale crosslinking with glutaraldehyde, or (ii) chelation reaction between chitosan and silver ion and finale a) reaction between chitosan chelate with silver ion and hyaluronic acid.

Regarding the chelation reaction, chitosan forms a complex with the silver ions that has modified physio-chemical properties and supermolecular structure. The supermolecular modification consists of a transformation of the chitosan molecules in solution from a helical structure to a random, disorganized form. This structure has the capacity to retain the silver ions by van der Waals and ionic forces. The physio-chemical modifications transforms the chitosan to a hydrogel. The degree of swelling of the hydrogel depends on the concentration of the silver nitrate solution and the reaction time. Hydrogel dimensional stability and control of the degree of hydrogel swelling is realized by two methods: (i) crosslinking with glutaraldehyde; and (2) coating the final layer of chitosan-$Ag^+$ with a polyionic complex with a base of chitosan-Ag+ and hyaluronic acid. The hydrogels discussed herein form irreversibly and may elute silver ions at a constant rate over time, such as 2 weeks.

Generally speaking, non-limiting factors that influence the preparation and properties of the chitosan-silver coated catheters include:

The physio-chemical characteristics of the chitosan: the molecular mass of chitosan is typically between 400,000 to 600,000 g/mol with a degree of acetylation (DA) of 18-20%.

The concentration of the chitosan solution: the concentration of chitosan in a solution of 1% acetic acid is typically between 1.4-1.8%. The higher the concentration, the thicker the coating.

The temperature of the chitosan solution: the temperature is typically 5° C. to ensure proper coating thickness.

The concentration of silver nitrate solution: the concentration of silver nitrate solution is typically between 14-16%.

The reaction time and temperature for the chitosan coating on the catheter and the silver nitrate is typically 24 hours at room temperature.

The setting time with a 1% glutaraldehyde solution is typically 8 min.

The drying time after the coating of the chitosan-silver complex is typically 24 hours.

Examples of methods of preparing coated catheters in accordance with these factors and the present invention are described below.

EXAMPLE 1

Preparation of Chitosan-$Ag^+$ Coated Catheters and Crosslinking with Glutaraldehyde Solution Preparations 1% (w/w) acetic acid solution: In a 1000 ml graduated flask, 10 g of concentrated acetic acid (98%) and 990 ml double distilled water (without $Cl^-$ ions) were combined.

1.8% (w/w) chitosan solution: In a 3 L mixer, 982 mL of 1% acetic acid solution and 18 g of chitosan (type VANSON with degree of acetylation (DA)=20% and a molar mass of 585,000 g/mol) were added. The solution was agitated until all of the chitosan was dissolved. The solution was centrifuged (3500 rpm) to eliminate possible microgels and colored particles. The solution was kept at 5° C.

14% (w/w) silver nitrate solution: Silver nitrate (35 g) and double distilled water were added to the fill mark of a 250 ml graduated flask. The solution was kept at room temperature and out of the light.

0.98% (w/w) glutaraldehyde solution: To a 200 ml graduated flask, 2 ml of aqueous 98% solution of glutaraldehyde were added. Double distilled water was added to the fill mark.

Step A: Application of the First Layer Comprising Chitosan-$Ag^+$

The surface of the catheters was first cleaned with a 98% solution of ethanol and finally dried. The thickness of the coating and the quantity of the silver contained depends on the concentration of the chitosan and silver nitrate solutions. With decreasing concentrations of chitosan solutions, the thickness of the hydrogel coating is decreased. This Example employed a 1.8% (w/w) chitosan solution and a 14% (w/w) silver nitrate solution.

A 100 ml cylinder was filled with a 1.8% (w/w) chitosan solution and kept at 5° C. The portion of the catheter to be coated was submerged into the solution and kept for 1 minute. The coated portion of the catheter was then introduced immediately into a precipitation tube that contained an 18% (w/w) silver nitrate solution. The catheters were held in this solution for 5 min. The catheter was then introduced into a second solution of 18% silver nitrate solution for 24 hours.

Step B: Application of the Second Layer Coat of Chitosan-$Ag^+$ complex to Form a Hydrogel Following the application of the first layer, and without drying, the catheter was rinsed in distilled water (without $Cl^-$) and dipped into a solution of 1.8% (w/w) chitosan at 5° C., and held for 1 minute. The second layer was deposited over top of the first layer. Immediately following this dipping step, the catheter was dipped into an 18% (w/w) silver nitrate solution and held for 1 minute for the first precipitation and then into a final solution of 18% (w/w) silver nitrate for 24 hours. The concentrations of the silver nitrate solutions were evaluated and corrected after every 3 to 4 uses.

The degree of hydrogel swelling varies from $\alpha=3000$ for reaction times of 3 hours to $\alpha=125$ for reaction times of 24 hours, where $\alpha$ represents the degree of swelling: $\alpha=((\text{equilibrium mass of the hydrated hydrogel}-\text{the dry weight of the hydrogel})/\text{the dry weight of the hydrogel} \times 100)$.

Step C: Crosslinking of the Catheter-deposited Chitosan-$Ag^+$ Hydrogels with Glutaraldehyde Following steps A and B, the prepared catheters were rinsed in distilled water and dipped into a 100 ml cylinder containing a 0.98% (w/w) solution of glutaraldehyde, and left for 8 minutes. The catheters were then given a final rinse in distilled water and then dried for 48 hours at room temperature.

EXAMPLE 2

Preparation of Catheters Coated with a Chitosan-$Ag^+$ Complex and Hyaluronate-$Ag^+$ Complex Solution Preparations 1% (w/w) acetic acid solution: See Example 1.

1.8% (w/w) chitosan solution: See Example 1.

16% (w/w) silver nitrate solution: In a 250 ml graduated flask, 40 g silver nitrate was added and double distilled water was added to the fill mark. The solution was kept at room temperature and out of the light.

1% (w/w) sodium hyaluronate solution: In a glass, 1 g of sodium hyaluronic acid and 99 g of water were added. The solution was agitated until the sodium hyaluronic acid was dissolved (around 3-4 hours). The solution was kept in the refrigerator, and was brought to room temperature before use.

Step A: Application of the First Coating Layer with a Chitosan-$Ag^+$ Solution

Comments on Procedure:

The catheters were cleaned with 98% ethanol prior to coating and dried. The thickness of the coating and the quantity of the silver contained depends on the concentration of the chitosan and silver nitrate solutions. With decreasing concentrations of chitosan solutions, the thickness of the hydrogel coating is decreased. This example employed a 1.8% (w/w) chitosan solution. The concentration of the silver nitrate solution can determine the concentration of the silver in the layers and the swelling properties thereof. Concentrations below 16% (w/w) silver nitrate are not recommended because the coating does not contain sufficient silver, the layer will swell in an aqueous solution, and the stability will be weak. To stabilize the layers under these conditions, crosslinking may be employed, such as with a 1% (w/w) solution of glutaraldehyde (see Example 1). Using a concentration of 16% (w/w) silver nitrate, for example, avoids the need to use a crosslinking agent in this manner.

Temperature is an additional factor regarding coating thickness. With increased temperature, the thickness of the layer is generally decreased. For example, a temperature increase from 5° C. to 20° C. results in a decrease in layer thickness by 50%. For silicone-, polyurethane- and PVC-based catheters, 5° C. is an exemplary temperature that may be employed. It is not recommended to use a temperature less than 0° C. or in the range of 0-3° C. because the thickness of the layer is significantly increased and it is difficult to control the uniformity of the layer thickness.

Method:

A 100 ml cylinder was filled with the chitosan solution and kept at 5° C. The portion of the catheter that is to be coated was submerged into the solution and kept for 1 minute. The coated portion of the catheter was then introduced immediately into a precipitation tube that contained an 18% (w/w) silver nitrate solution. The catheters were held in this solution for 5 minutes. The catheter was then introduced into a second solution of 18% (w/w) silver nitrate solution for 24 hours.

Step B: Application of the Second Coating Layer of Chitosan-Ag$^+$ Solution to Form a Hydrogel See Step B of Example 1 above.

Step C: Application of the Third Coating Layer of a Chitosan-Ag$^+$ Sodium Hyaluronate-Ag$^+$ Ion Complex Comments on Procedure:

The application of a superficial layer of hyaluronic acid-chitosan-Ag$^+$ has the advantage of augmenting the elasticity of the catheters in a humid environment and diminishes the degree of swelling of the chitosan-Ag$^+$ layers deposited in steps A and B. This layer also increases the biocompatibility and the superficial concentration of silver ions.

Method:

After step B, the catheters were dipped into a 1% (w/w) solution of sodium hyaluronate and kept for 4 hours. During this period, the chitosan-hyaluronate complex is formed. The catheters were then treated with a 16% (w/w) solution of silver nitrate for 10 minutes. The catheters were then dried for 48 hours.

Experimental Procedures to Confirm Effectiveness

The following examples are presented as non-limiting examples of procedures to test the methods and apparatus disclosed in this specification.

EXAMPLE 3

Direct Daily Dosing at Low Levels

These experiments were carried out in order to determine if low doses of sclerosing agents could result in successful pleurodesis when administered in a repeated fashion. Using daily doses of silver nitrate or doxycycline in decreasing doses starting at the lower limit of what has previously been reported to be effective, further decreases in dosing were administered utilizing single day, 5 day or 14 day regimens. Theoretically utilizing lower doses on a repeated basis may reduce the frequency and/or severity of side effects.

All experiments were carried out in a rabbit model of pleurodesis which has been extensively utilized in the field of pleurodesis in many centers around the world. As explained in further detail below, standard pleurodesis is score graded one to 8 and is used for assessment of the efficacy of pleurodesis, the number one representing a normal pleural space while 8 represents complete pleural symphysis. A score of 5 or higher is usually considered consistent with a successful pleurodesis.

Doxycycline Methods

A total of 18 animals were treated with doxycycline at doses of 1 mg/kg, 5 mg/kg, or 10 mg/kg. Animals (n=2) in the 10 mg/kg group received only the single day injection, animals (n=2/group) in the 5 mg/kg range received either 1 day, 5 days or 14 days injection, and animals in the lowest dose range of 1 mg/kg (n=2/group) received repeated injections over 5 days or 14 days. The results were compared with the placebo groups (n=2/group) which were given saline injections over either 1, 5 or 14 days. All doses were administered after a daily drainage. At the end of the treatment period, the animals were euthanized and pleurodesis was scored according to the standard scoring system shown in FIG. 5.

Results with Doxycycline

Figures 3C, 4A:
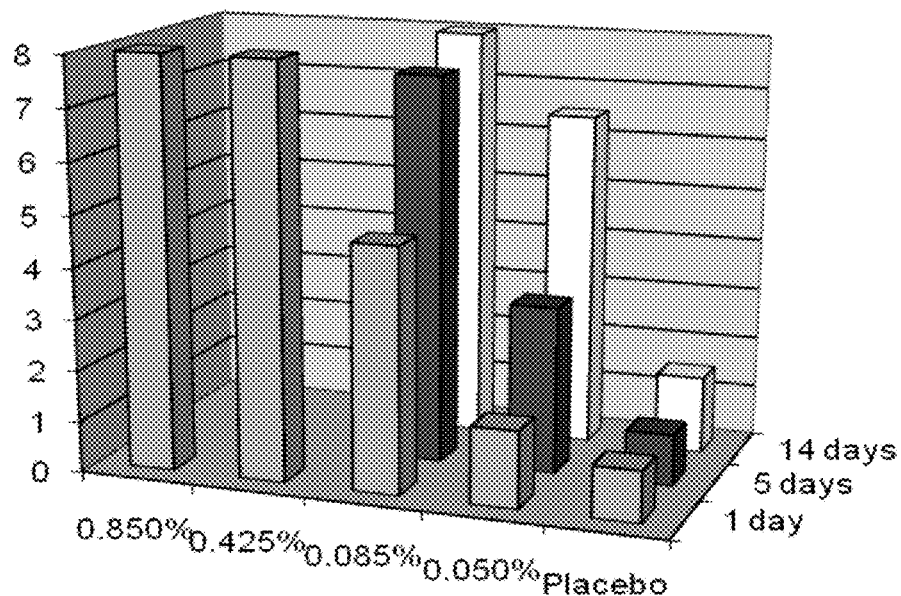
Figures 4B, 4C:
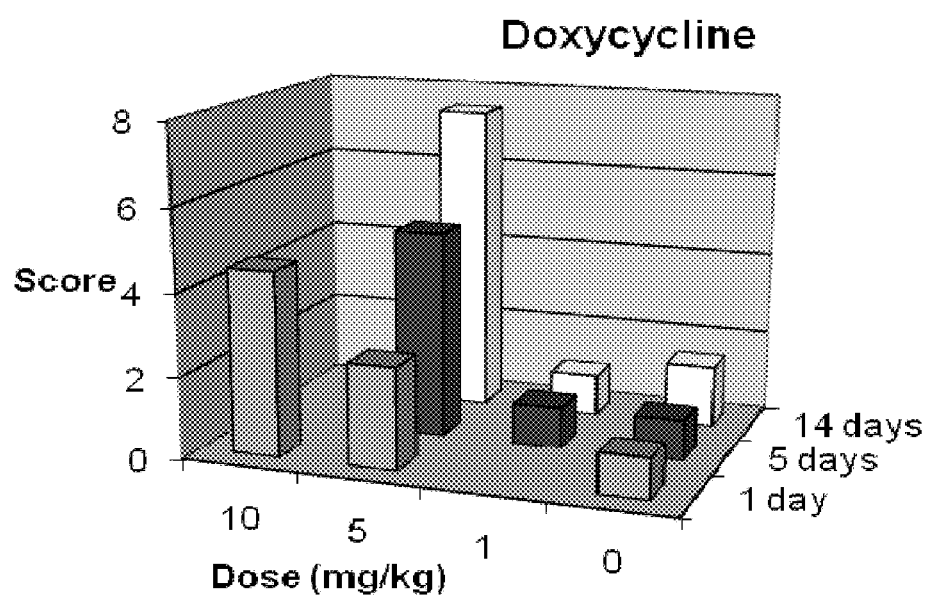

FIG. 4A provides a table with experimental results of individual specimens using doxycycline, while FIG. 4B provides a table summarizing the average pleurodesis scores for the specimens based on different concentrations and days of administration. FIG. 4C provides a graphical representation of the results provided in FIG. 4B.

The lowest reported effective dose for doxycycline in this model is 10 mg/kg as a single dose. In our initial experiments this dose resulted in a mean score of 4.5. Using half this dose at 5 mg/kg repeated over 5 days did not result in pleurodesis although a score of 5 was obtained when this dose was used over 14 days. An even lower dose of one mg/kg was ineffective at causing pleurodesis whether given over 5 days or 14 days. As such, for doxycycline a 50% reduction in individual dose can still achieve pleurodesis when repeated over two weeks. Whether this modest daily dose reduction would lead to significant reduction in side effects is unknown.

Silver Nitrate Methods

A total of 20 animals were treated with silver nitrate at dosing concentrations of 0.05%, 0.085%, 0.425% and 0.85%. Note that reported effective single dose injections of silver nitrate in this model range from 0.3% to 0.5%. A concentration of 0.25% was reported to be ineffective in one publication, but overall data is limited. The groups were assigned a treatment period of either a 1 day, 5 days or 14 days of repeated injections. A minimum of 2 animals were used for each of the 10 groups, and a further 2 animals were tested at the lowest dose range (0.05%). See Table 2. The results were compared with the placebo groups which were given saline injections over either 1, 5 or 14 days (n=2/group). All doses were administered after a daily drainage. At the end of the treatment period, the animals were euthanized and pleurodesis was scored according to the standard scoring table (shown in FIG. 5). Degree of pleural inflammation and fibrosis was also evaluated.

Results with Silver Nitrate

FIG. 3A provides a table with experimental results of individual specimens using silver nitrate, while FIG. 3B provides a table summarizing the average pleurodesis scores for the specimens based on different concentrations and days of administration. FIG. 3C provides a graphical representation of the results provided in FIG. 3B. As illustrated in FIGS. 3A-3C, successful pleurodesis scores (greater than or equal to 5) were achieved at concentrations of 0.050% when the dosage was administered for 14 days. In addition, successful pleurodesis scores were achieve at concentrations of 0.085% when the dosage was administered for 5 days.

Excellent pleurodesis (average score of 8/8) was achieved with a single day injection at a dose of 0.85% and 0.425% consistent with prior publications. In contrast, a lower dose of 0.085% was ineffective in achieving pleurodesis as a single dose but effective when repeated daily over 5 days (average score 7.5/8), and the lowest dose of 0.05% only effective in the group receiving 14 days of repeated injections (average score 6.5/8). The trends clearly suggest that at low doses, multiple days of treatment are necessary to achieve effective pleurodesis with silver nitrate.

One advantage of such a dosing regimen may relate to a reduction in side effects. Side effects associated with current methods of pleurodesis can be both distressing and dangerous. Intense pain has been reported after the administration of intrapleural tetracycline (Light et al., 1990), and has also been reported to be significant with doxycycline (Heffner et al., 1994; Mansson, 1988; Herrington et al., 1996; Pulsiripunya et al., 1996), talc (Thompson et al., 1998; Marom et al., 1999; Brant and Eaton, 2001; Stefani et al., 2006) and silver nitrate (Wied et al., 1981). Intrapleural local anesthetics may reduce pain (Sherman et al., 1988), but narcotic analgesic agents are almost always required (Elpern et al., 1994).

Data exists suggesting that untoward effects of sclerosing agents can be dose dependent. In an animal model, increasing doses of TGF beta beyond what is required for pleurodesis results in an increase in the volume of pleural fluid formed (Light et al., 2000). As well, animals treated with a higher dose developed contralateral pleural fibrosis as well as peritoneal inflammation suggesting systemic toxicity. In another study, animals receiving higher doses of intrapleural minocycline had excess mortality (Light et al., 1994). In a similar model, it was shown that animals receiving high doses of talc intrapleurally had higher rates of talc deposition in the lung, mediastinum, pericardium and liver. In addition, the systemic inflammatory response was significantly higher with higher doses of talc (Montes et al., 2003). Clinical cases of ARDS following talc administration has been associated by some to the higher doses used (Rinaldo et al., 1983; Kennedy et al., 1994).

In the case of silver nitrate in particular, it has been shown that a concentration of 0.1% resulted in less systemic response in terms of white blood cell count elevation and neutrophilia, as well as a serum interleukin-8 and VEGF levels than at the 0.5% dose (Marchi et al., 2005). In addition, a human trial has demonstrated that a 0.5% concentration was well tolerated by patients (Paschoalini et al., 2005) while this agent had been abandoned by clinicians several decades previously because of severe pain and side effects associated with concentrations of up 10% (Wied et al., 1981; Wied et al., 1983).

Conclusions

These experiments suggest that repeated administration of sclerosing agents at doses considered subtherapeutic when administered as a single dose can still be effective in causing effective pleurodesis. Silver nitrate in particular appears to offer the possibility of large dose reductions while maintaining its effect if administered over 14 days.

EXAMPLE 4

Coated Catheter Dosing, Rabbit Model

Treatment of pleural effusions often consists of attempts at creating a pleural symphysis with a sclerosing agent, usually administered as a single bolus dose. As demonstrated above, low dose repeated administration of silver nitrate (SN) (as compared to single high dose administration) can lead to effective pleurodesis. The objective of this study is to demonstrate effective pleurodesis with a sustained release catheter that elutes a low dose of silver nitrate continuously over 14 days.

The study consisted of an in-vivo experiment with 3 groups of 6 rabbits in a well-described animal model for pleural disease. The study consisted of placement of a SN coated catheter in the pleural space and a placebo/uncoated catheter in controls. The contralateral pleural space for each animal served as additional controls.

The animals underwent placement of a small bore intrapleural catheter under general anesthesia. The catheters were either uncoated, coated with 24 mg SN, or coated with 50 mg SN and placed in the right pleural space. One animal in the 50 mg group did not complete the study. The catheters were aspirated daily for 14 days to remove any pleural fluid, and were removed on day 15 and necropsy performed on day 29. Efficacy of pleurodesis was assessed by a 1-8 score (1-normal, 8-pleural symphysis greater than 50% hemithorax), with a score of greater than or equal to 5 considered significant (FIG. 5).

Experimental Procedure: Pleural Catheter Placement— Rabbits

SPF New Zealand white rabbits weighing 1.5 to 2.0 kg were utilized. All animals were housed to minimize exposure to pathogens. Animals were cared for as per standard operating procedures.

Animals received duprenorphine 0.02-0.05 mg/kg sc preoperatively and anesthesia was induced with an inhalational agent.

Animals were clipped and prepped. The right lateral and posterior chest wall and back required clipping and, after the induction of anesthesia, the animal was placed in the left lateral decubitus position prior to the scrub and prep procedure. Supplemental oxygen was administered by mask. A polyethylene tube (described below) was inserted into the right pleural space as follows. A 1 cm skin incision was made with a scalpel over the lateral right chest 5 cm lateral to the vertebral line and 2 cm proximal to the costal margin. The subcutaneous fascia was grasped with forceps and cut with a scissor creating a 0.5 cm opening. Blunt dissection was used to enter the pleural space with a small curved forceps thereby avoiding injury to the underlying lung. The chest tube was then gently advanced anteriorly through the opened forceps to a distance of 5-6 cm. The tube was aspirated with a syringe in order to confirm patency and resorb any air which may have entered the pleural cavity during catheter insertion. As well, the proximal end of the catheter was tunneled under the skin to the back of the animal and sutured to prevent migration. This was performed by making a 0.5 cm skin incision at the base of the neck in the midline, followed by passage of a strait forceps subcutaneously in a caudal direction and then lateral to the site of catheter insertion. The proximal end of the tube was then pulled back with the forceps to exit at the small neck incision. A needleless IV adapter was attached to the proximal end of the tubing and the tube was once again aspirated to ensure patency and absence of a pneumothorax. A suture was applied to the neck incision and wrapped around the needleless IV port to keep it in position. The chest wall, fascia and skin at the insertion site was closed, each with two to three 2.0 silk sutures.

The animals were returned to the isolation area once recovery had occurred. Analgesia with duprenorphine 0.02-0.05 mg/kg sc q8-12 h was provided as needed during the study period if evidence of pain such as anorexia, teeth grinding, guarding surgical site or agitation was observed.

Catheter Configuration

Catheters were constructed from medical grade polyethylene tubing (inner diameter 1.58 mm, outer diameter 3.18 mm). The catheter coating was applied over the distal 3 cm to deliver a dose of SN previously determined to lead to effective pleurodesis over a 14 day period (24 mg over 14 days). The study was repeated with a higher dose catheter (50 mg over 14 days) as well. Additional drainage side holes were incorporated just proximal to the coating to facilitate drainage. The catheters were sterilized by ethylene oxide gas and packaged in a sealed and sterile package. The proximal end of the tubes was fitted with a sterile access/valve system at the time of placement.

Clinical Care and Monitoring

All animals were cared for as per standard operating procedures. Animals were assessed for general well being on a daily basis. Their weight was measured on day 1, 8, 15, 22 and 29 of study. Daily clinical observations and clinical examinations by the veterinarian staff were performed prior to treatment, and at days 1, 8, 15, 22 and 29. Fluid was aspirated from the pleural catheter on a daily basis and the volume of fluid withdrawn documented. The pleural catheter was maintained for 14 days.

Euthanasia & Necropsy

Animals were euthanized on day 29 of the study with the injection of 3 mL Euthanyl™ (pentobarbital 240 mg/mL) intravenously into the marginal ear vein. Animals dying or requiring euthanasia prior to day 29 underwent necropsy examination.

The thorax was removed en bloc. The trachea was entered with a needle attached to a syringe filed with 50 ml of 10% formalin in phosphate buffered saline which was injected in the trachea to inflate the lungs. After the inflation, the trachea was ligated with nylon suture ties and the entire thorax submerged in a 10% formalin solution for at least 48 h. Each pleural cavity was then exposed by making bilateral incisions through the diaphragms and through all the ribs at the midclavicular line. In this manner, the sternum and the medial portions of the anterior ribs were removed, so that the lung and pleural cavities could be evaluated. The presence or absence of hemothorax (clotted blood in the pleural cavity), and the position of the mediastinum in each animal, were recorded. Macroscopic examination of the pleural was performed and graded according to an 8 point scale (see FIG. 5; see also Lee, Teixeira, Devin, et al. *Transforming Growth Factorbeta 2 Induces Pleurodesis Significantly Faster than Talc,* 163 AM. J. OF RESPIRATORY AND CRITICAL CARE 640 (2001), incorporated herein by reference). Samples for histopathological assessment were taken from pleura, lung and diaphragm bilaterally.

Pathology

Samples obtained at necropsy were fixed as per the standard neutral buffered formalin fixation protocol. Hematoxylin and eosin (H & E) and Musto stains were applied to the histologic sections.

The pleural fibrosis was graded as none (0), equivocal (1), mild (2), moderate (3), or severe (4).

Statistical Analysis
 a. Data analysis: Mean values for pleurodesis scores and lab values were calculated. Descriptive terms were used for pathological analysis.
 b. Statistics: Comparison of the mean pleurodesis score between the treatment and control groups were compared with a t-test. Using groups of 6 animals allows the detection of a difference in pleurodesis score from 2 to 6 (i.e. 4 points difference, with a SD of 2) with an alpha of 0.05 and beta of 0.9.

Ethics

The study was approved by the Animal Care Committee at the University of Calgary. All precautions were taken to ensure that the investigators comply stringently with the regulations for ethical treatment of animals in experimental research.

Results

Figure 6:
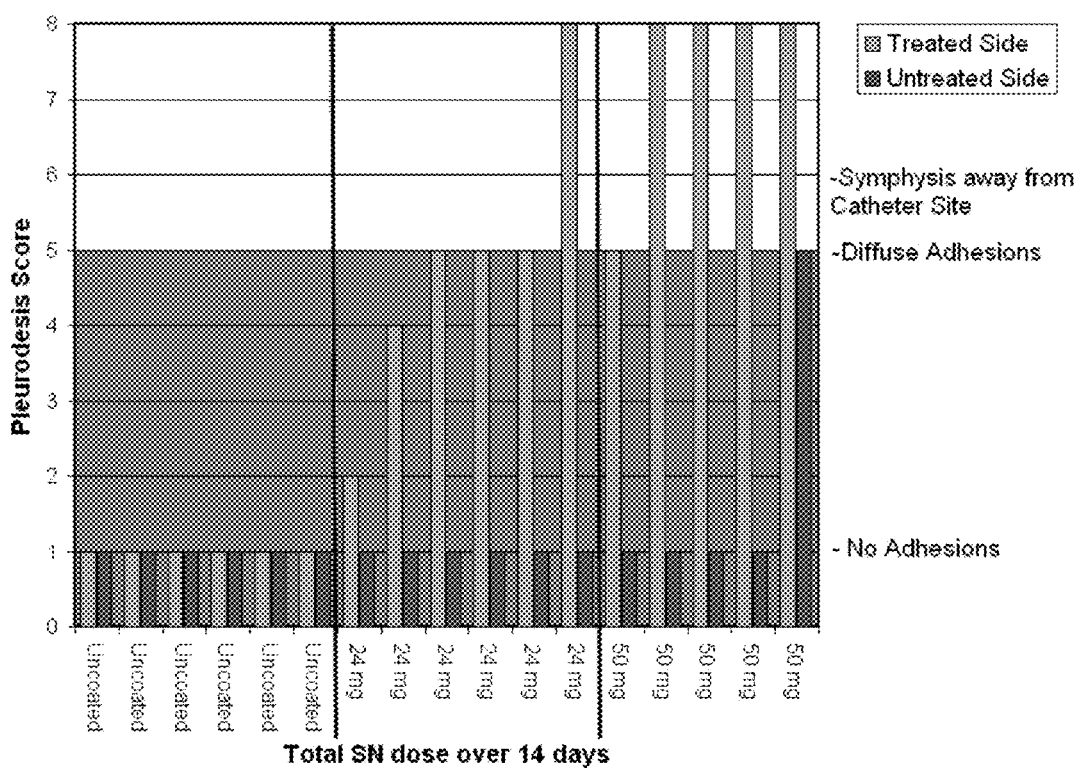
FIG. 6 illustrates a graph of experimental test results from a coated catheter dosing study using a small animal model.
Figures 7, 8:
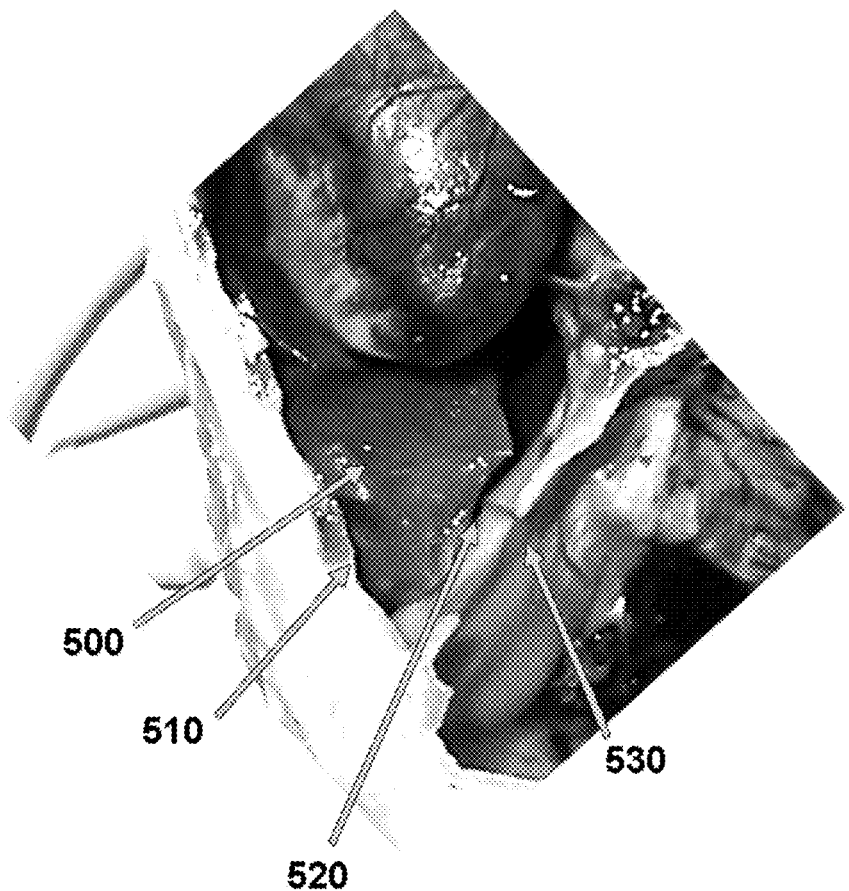
FIG. 7 illustrates a table of experimental test results from a coated catheter dosing study using a small animal model.
FIG. 8 is a photograph demonstrating the gross pathology of an animal specimen with a pleural space used as a contralateral control

Results from a test conducted in accordance with the procedure explained above in Example 4 are provided below in FIG. 6. These results demonstrate that pleurodesis was successfully achieved in each animal that was treated with a silver nitrate coated catheter, which sustainably released 50 mg of silver nitrate over a 14 day period in vivo (score greater than or equal to 5). In the group in which the catheter sustainably released 24 mg of silver nitrate over a 14 day period, 4 of the 6 animals achieved successful pleurodesis. FIG. 7 illustrates a table of the average pleurodesis scores achieved for the various dosage levels.

FIG. 8 is a photograph demonstrating the gross pathology of an animal specimen with an unfused pleural space used as a contralateral control. In FIG. 8, a lung 500 is visible next to a chest wall 510 and a diaphragm 530. As shown in FIG. 8, pleural space 520 (between lung 500 and diaphragm 530) is not fused and does not show adhesions. In this example, no catheter has been inserted and no sclerosing agent has been introduced. Consequently, the pleural space is visible in its "normal" condition.

Figure 9A:
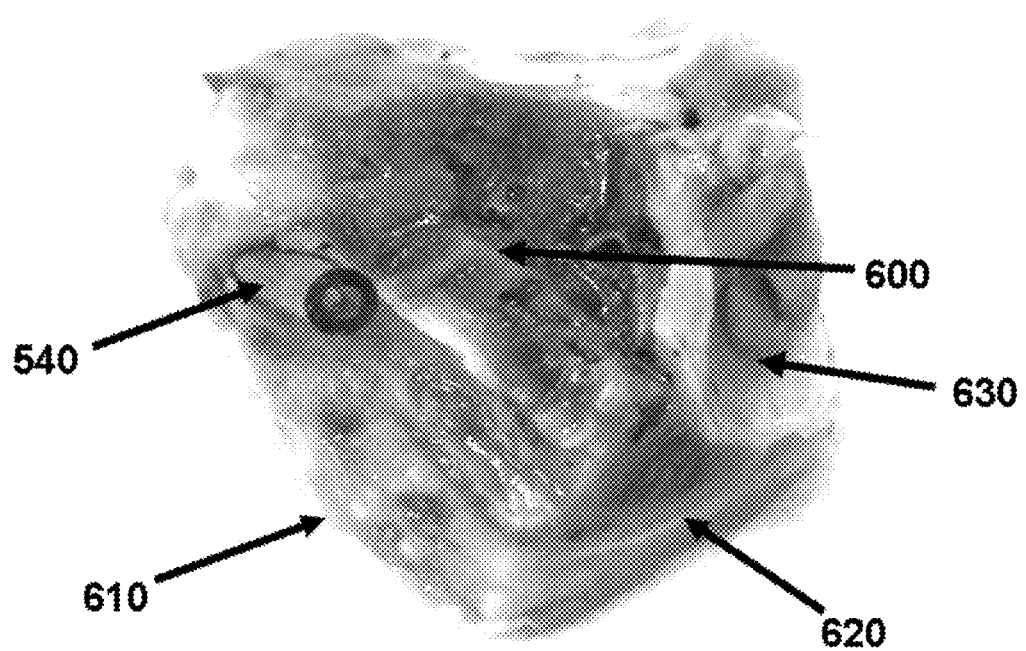
FIG. 9A is a photograph demonstrating the gross pathology of an animal specimen with a pleural space treated by a sustained release catheter.

FIG. 9A is a photograph demonstrating the gross pathology of an animal specimen with a fused pleural space. As shown in FIG. 9A, a sustained release catheter 540 has been inserted into a pleural space surrounding a lung 600 that is next to a chest wall 610 and a diaphragm 630 according to the procedure described above for Example 4. In this particular specimen, catheter 540 was coated with silver nitrate and delivered a dose of approximately 50 mg over a 14 day period. As shown in FIG. 9A, pleural space 620 has been fused and effective pleurodesis achieved with the sustained release of silver nitrate from catheter 540. Pleural space 620 exhibits diffuse pleurodesis with a majority of the pleural layers fused, and adhesion of the pleural layers in areas that are located away from catheter 540.

Figure 9B:
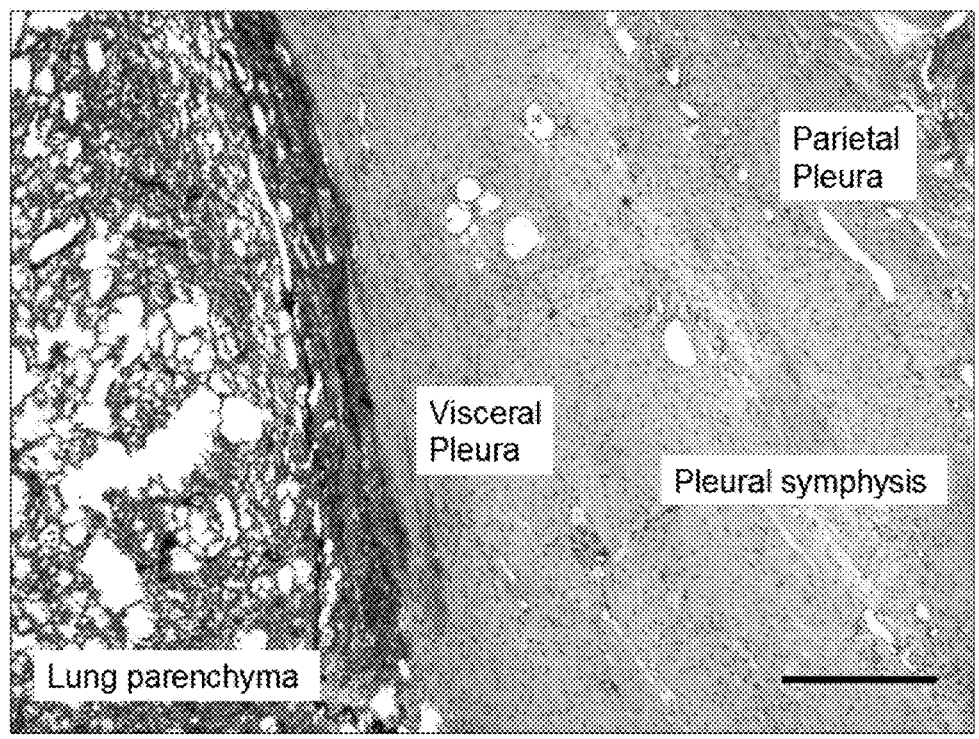
FIG. 9B is a microscopic image of pleurodesis in the pleural space of an animal specimen treated with a sustained release catheter.
Figure 9C:
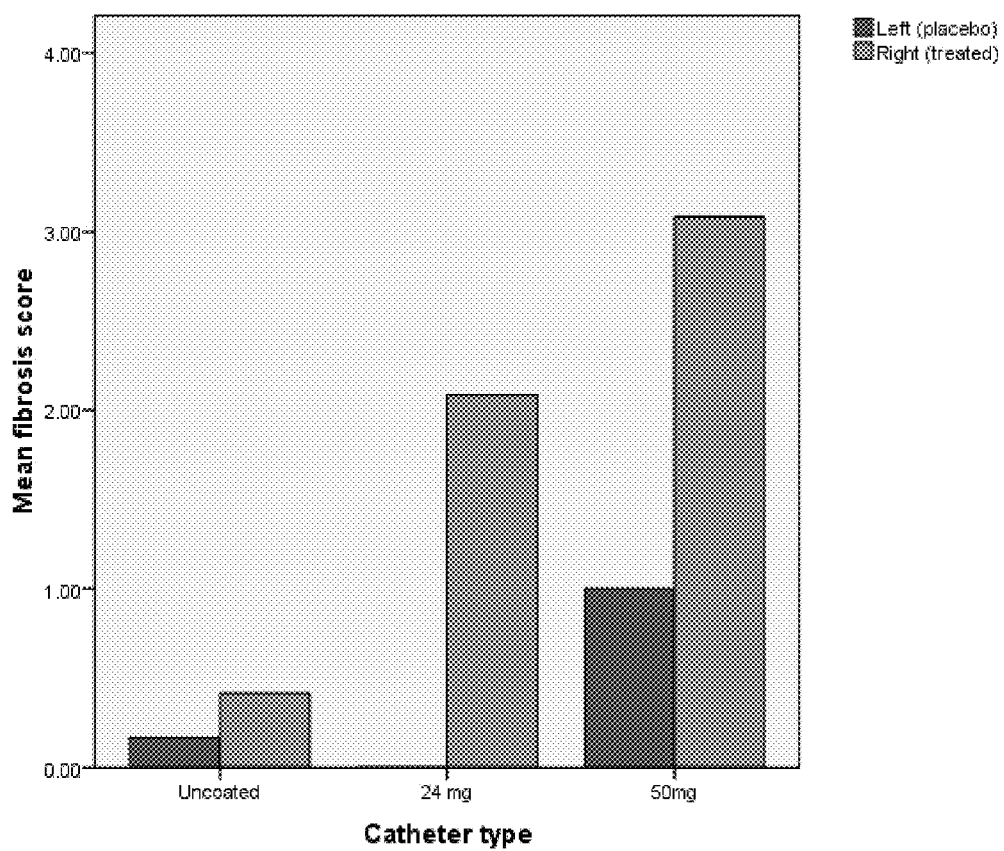
FIG. 9C is a graph showing histopathological fibrosis scores of treated and untreated control pleural spaces for each treatment group.

FIG. 9C demonstrates that the histological fibrosis score (0-4 scale) was significantly higher for the right pleural space in animals receiving a coated catheter (24 mg or 50 mg) as compared to the uncoated catheters (p<0.05) as well as when compared to the contralateral (left) control pleural space (p<0.05). FIG. 9B represents a histological section (Musto stain) of lung and pleural space demonstrating extensive fibrosis (grade 4) and resulting in pleural symphysis in an animal treated with a 50 mg coated catheter.

EXAMPLE 5

Coated Catheter Dosing, Sheep Model

The objective of this study is to demonstrate effective pleurodesis with a sustained release catheter that elutes a low dose of silver nitrate consistently over 14 days in a large animal model.

Experimental Procedure: Pleural Catheter Placement—Sheep

The study consisted of an in-vivo experiment in groups of four sheep consisting of placement of a SN coated catheters in the right pleural space. Four control animals underwent chest tube placement without the drug eluting coating. The contralateral pleural space for each animal served as additional controls.

Daily monitoring of vital signs, including weight, was performed. The animals were euthanized on day 29 and necropsy performed, including microscopic examination of the pleura, lung. A third group of four animals underwent placement of a coated catheter with a 25% decrease in dose as pleurodesis score was greater than 5 at the initial dose tested.

A well described animal model for pleural disease and pleurodesis using yearling sheep (Suffolk) weighing 25-30 kg was used. (Lee, et al., 2002; Lee et al., 2000). A total of 12 animals were required to complete the study. All animals were housed to minimize exposure to pathogens. Animals were cared for as per standard operating procedures.

Animals were bathed and sheared. General anesthesia was induced via inhalation. The circumference of the chest wall and back was clipped and, after the induction of anesthesia, the animal placed in the left lateral decubitus position prior to the scrub and prep procedure. Supplemental oxygen was administered by mask. A sterile pleural catheter designed from medical grade silicone tubing with an additional side hole was inserted into the right pleural space as follows. A 3 cm skin incision was made with a scalpel over the lateral right chest 15-20 cm lateral to the vertebral line at the 7th intercostals space. The subcutaneous fascia was grasped with forceps and cut with a scissor creating a 0.5 cm opening.

Blunt dissection was performed to enter the pleural space with a curved blunt forceps thereby avoiding injury to the underlying lung. The tubing was then gently advanced anteriorly through the opened forceps to a distance of 10-15 cm. The tube was aspirated with a syringe in order to confirm patency and resorb any air which may have entered the pleural cavity during catheter insertion.

In addition, the proximal end of the catheter was tunnelled under the skin to the back of the animal and sutured to prevent migration. This was performed by making a 1 cm skin incision at the level of the vertebral bodies in the midline, followed by passage of a strait forceps subcutaneously in a posterior direction and then lateral to the site of catheter insertion. The proximal end of the tube was then pulled back with the forceps to exit at the back incision. A needle-less IV adapter was attached to the proximal end of the tubing and the tube once again aspirated to ensure patency and absence of a pneumothorax. A suture was applied to the back incision and wrapped around the needle less IV port to keep it in position. The chest wall, fascia and skin at the insertion site were closed, each with 2 to 3 2.0 silk sutures. The animals were returned to their housing area once recovery has occurred. Analgesia with buprenorphine 0.01-0.02 mg/kg sc q6-8 h was provided as needed during the study period if evidence of pain such as anorexia, teeth grinding, guarding surgical site or agitation was noted.

Catheter Configuration

Catheters were constructed from medical grade silicone tubing of 4.88 mm outer diameter (surface area 1.533 cm$^2$ per cm of tubing). The catheter coating was applied over the distal 13 cm in such a way to deliver the dose of SN over a 14 day period. The dose of silver nitrate has been extrapolated from previous experiments in a rabbit model. While there are no studies with single dose silver nitrate reported in sheep, other pleurodesis agents appear to be effective at doses similar to those used clinically. A total 14 day dose of 1,000 mg of silver nitrate was used for the first 4 treated animals. Given its effectiveness, an additional group was treated at a reduced dose of 750 mg.

An additional drainage side hole was incorporated just proximal to the coating to facilitate drainage. The catheters were sterilized by ethylene oxide gas and packaged in a sealed and sterile package. The proximal end of each tube was fit with a sterile access/valve system at the time of placement.

Clinical Care and Monitoring

All animals were cared for as sheep husbandry standard operating procedures. Animals were assessed for general well being on a daily basis. Weights were measured on day 1, 8, 15, 22 and 29 of study. Daily clinical observations and clinical examinations by the veterinarian staff were performed prior to treatment, and at days 1, 8, 15, 22 and 29. Fluid was aspirated from the pleural catheter on a regular basis and the volume of fluid withdrawn documented. The pleural catheters were maintained for a minimum of 14 days and until fluid withdrawn became less than 20 ml/sheep per day for 2 consecutive days.

Euthanasia & Necropsy

Animals were euthanized on day 29 of the study with Euthanyl-Forte (pentobarbital 540 mg/mL, 10 ml per 50 kg) intravenously into the jugular vein while manually restrained. At the time of autopsy, the thorax was opened ventrally and the pleural cavities exposed. The degree of macroscopic pleurodesis was assessed according to the 8 point scoring system shown in FIG. 5. Samples of visceral pleura, diaphragm and lung were obtained bilaterally and placed in 10% formalin in phosphate buffered saline.

Statistical Analysis a. Data analysis: Mean values for pleurodesis scores and lab values were calculated.
b. Statistics: Comparison of the mean pleurodesis score for a given agent at a particular dose was compared to the appropriate control with a t-test. Using groups of 4 animals allowed the detection of a difference in pleurodesis score from 1.5 to 6 (i.e., 4.5 points difference, with a standard deviation of 3) with an alpha of 0.05 and beta of 0.8.

Results

Figures 10, 11:
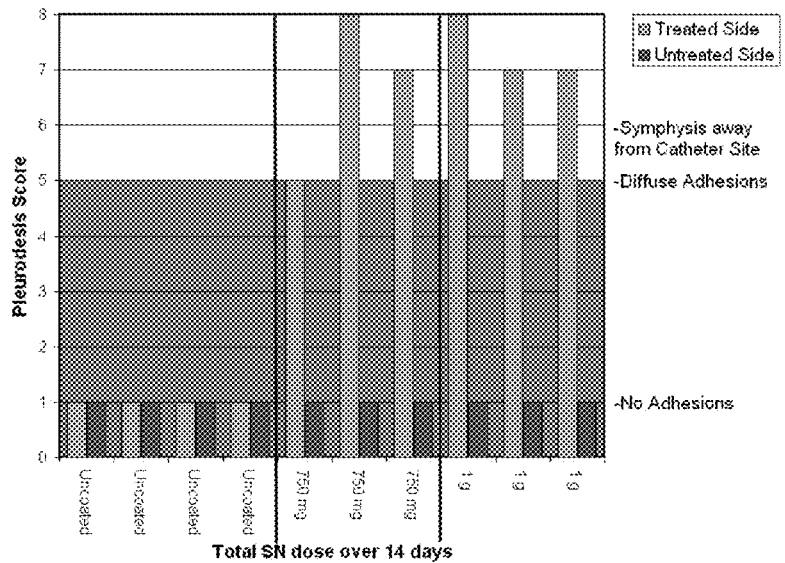
FIG. 10 is a table of pleurodesis scores for large animals treated with silver nitrate sustained release catheters.
FIG. 11 is a graph of pleurodesis scores for individual large animals treated with silver nitrate sustained release catheters.

Mean pleurodesis scores on the treated (right) side were 1.0, 6.67 and 7.33 for the uncoated, 750 mg and 1 g groups, respectively (p=0.001 vs. uncoated for each SN group). In the 1 g group, all 3 animals showed many diffuse adhesions between the visceral and parietal pleura away from catheter site with symphysis of the hemithorax away from the catheter site Each specimen in the 1 g group exhibited a score of 7 or greater, according to the scoring system explained in FIG. 5. Scores for the untreated (left) side were 1.0 for all groups. FIGS. 10 and 11 provide tabular and graphical data, respectively, illustrating the pleurodesis score for each animal in the study.

Demonstration of Sustained Release Properties

Experiments were conducted to demonstrate the effective sustained release of silver nitrate from catheters that were coated with silver nitrate according to the methods provided in this disclosure. The elution kinetics of a drug from a sustained release coating can be measured either in vivo or in vitro. (Spador, et al., 1974; Schaeffer, et al., 1988; Maki, et al., 1988; Groeger, et al., 1993; Raad, et al., 1996). The catheters used in the in vitro demonstration method described below were equivalent to the catheters utilized in the in vivo experiments described above.

The standard in vivo method of measuring drug kinetics introduced to the system (generally by oral administration) is to measure the quantity of the drug in the circulatory system. This method is generally considered the most precise and provides an accurate portrayal of how the medication is diffused in the system. However, in the treatment of pleural disease, systemic or intravascular absorption is not the desired result, so this method is not relevant.

The in vitro method is a more basic, but accepted method of measuring the release kinetics. The sample is introduced in a solution (usually held at a pH 5 or 7) and the amount of drug eluted is measured at regular time intervals (1-10). The amount of eluted drug is then calculated from the following equation:

$$m_{SN} = C_{SN}V_e + \Sigma_{i=0}^{n-1} C_i V_i \qquad (\text{Eq. 1})$$

Where:

$m_{SN}$=amount of silver nitrate (SN) released from the sample at a certain time (mg);
$C_{SN}$=concentration of silver nitrate (SN) in the extracted sample (mg/ml);
$V_e$=volume of elutent recirculated through the system (ml);
$V_i$=volume of the extracted sample, i, (ml);
$C_i$=concentration of silver nitrate (SN) in the extracted sample, i, (mg/ml).

Measurement Procedures 50 ml of distilled water and a known mass of dried hydrogel/silver coated catheters were placed in a container and protected from light. The system was held at a temperature of 37° C. and set at an agitation of 55 rpm.

Following the first hour, 2 ml of solution was removed by pipette, and immediately replaced with 2 ml of water (or solvent). For in vitro testing, distilled water was used to test the elution rate of the hydrogel/silver coated catheters because physiologic liquids produce a precipitation of free silver and also deposits on the surface of the catheter a layer of protein that can modify the kinetics. In an in vivo setting, the protein/silver complex is decomposed, the silver nitrate is found in its molecular form and the kinetics are undisturbed. The concentration of $AgNO_3$ in the solution was measured at each time point by two different methods: (1) Electrochemical: the ASV method (Anode Stripping Voltammetric) and (2) Atomic absorption: the AAS method (Atomic Absorption Spectroscopy).

Release Kinetics of Silver Ions from Polyurethane Catheters

Figure 12:
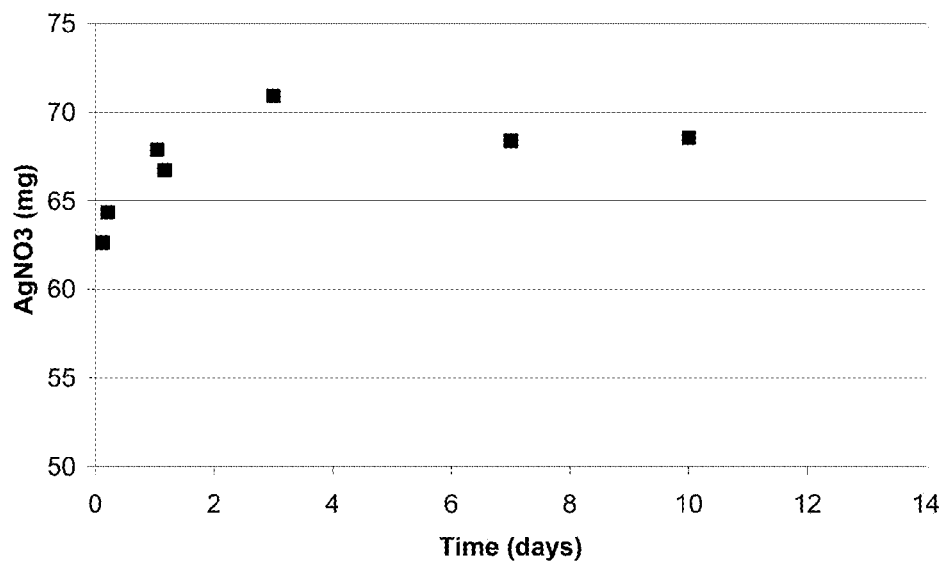
FIG. 12 is a graph illustrating the release kinetics of a polyurethane catheter coated with chitosan-silver nitrate gels.

An example of the kinetics of diffusion of silver nitrate from a polyurethane catheter coated with the hydrogel/silver coating is presented in FIG. 12. As shown in the figure, the amount of silver nitrate eluted from the catheter remained fairly constant over a 10 day period.

Figure 13:
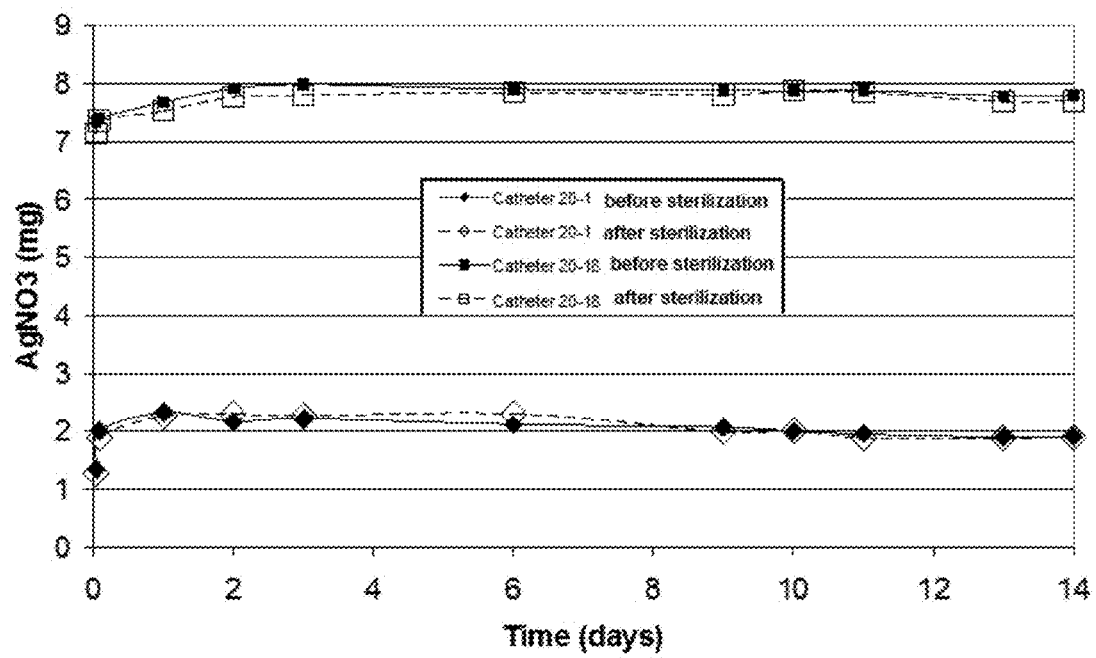
FIG. 13 is a graph illustrating the release kinetics of a polyurethane catheter coated with chitosan-silver nitrate gels.

As shown in FIG. 13, sterilization with ethylene oxide did not decrease the amount of silver nitrate on the catheters, nor did it modify the release kinetics.

Release Kinetics of Silver Ions from Silicone Catheters

Figure 14:
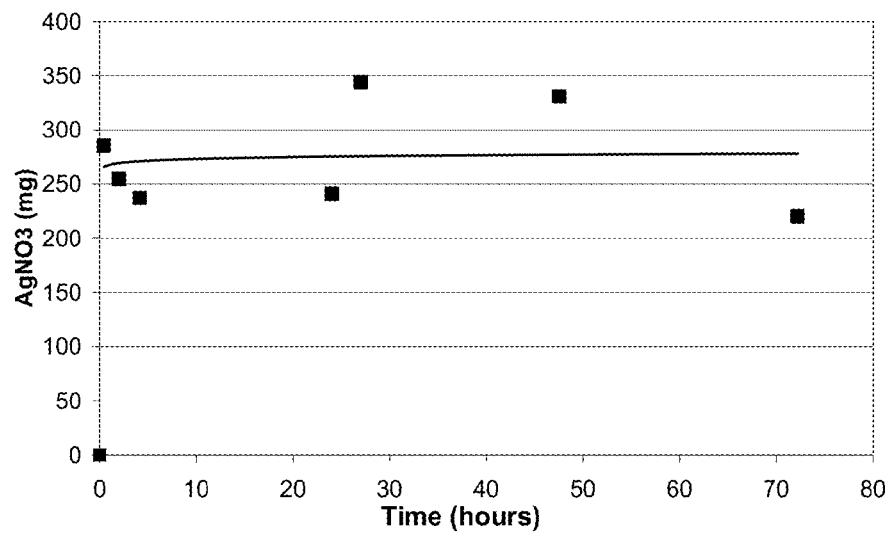
FIG. 14 is a graph illustrating the release kinetics of a silicone catheter coated with chitosan-silver nitrate gels.
Figure 15:
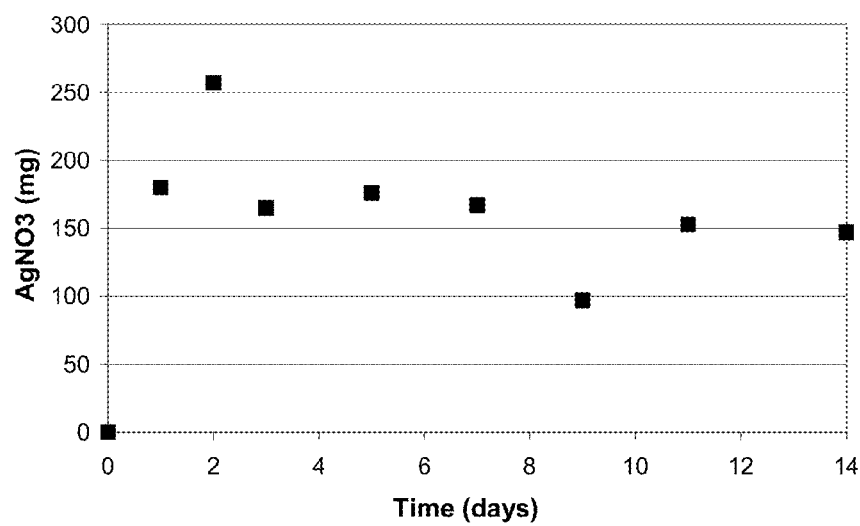
FIG. 15 is a graph illustrating the release kinetics of a silicone catheter coated with chitosan-silver nitrate gels.

In addition to the polyurethane catheters described above, silicone catheters with an external diameter of 4.88 mm (external surface area of 1.533 $cm^2$ per cm of tubing) were also used. The silicone catheters were coated over a length of 13 cm. Two different doses of catheters were prepared, Si5A and Si5B. Si5A provides a constant elution of approximately 250 mg silver nitrate for 13 cm of coated catheter over a 10 day period, which FIG. 14 demonstrates over the initial 3 day period. Si5B provides a constant elution of approximately 150 mg for 13 cm of coated catheter, and FIG. 15 demonstrates this constant elution over the full 14 day period. During experimental testing it was observed that approximately twenty percent of the silver nitrate remained on the catheter after the 14 day test period (resulting in an average release rate of approximately 5.7% of the silver nitrate per day).

Reference List

Each of the following references are incorporated herein by reference.
U.S. Pat. 4,265,848
U.S. Pat. 4,496,464
U.S. Pat. 5,304,121
U.S. Pat. 5,344,401
U.S. Pat. 5,576,072
U.S. Pat. 5,662,960
U.S. Pat. 5,674,192
U.S. Pat. 5,709,672
U.S. Pat. 5,733,496
U.S. Pat. 5,954,706
U.S. Pat. 6,221,425
U.S. Pat. 6,287,285
U.S. Pat. 6,409,716
U.S. Pat. 6,541,116
U.S. Pat. 6,645,547
U.S. Pat. 6,656,517
U.S. Pat. 6,719,991
U.S. Pat. 6,897,349
U.S. Pat. 6,916,379
U.S. Pat. 7,048,962
U.S. Patent Publn. 20060025816
U.S. Patent Publn. 20060116721
American Thoracic Society, *Am. J. Respir. Crit. Care Med.*, 162(5):1987-2001, 2000.
Bambauer et al., *ASAIO J.*, 303-308, 1998.
Bouros et al., *Chest*, 118:577-579, 2000.
Brant and Eaton, *Respirology*, 6(3):181-185, 2001.
Dumitriu et al., *Clin. Materials*, 6:265-276, 1990.
Dumitriu et al., *J. Bioactive Compat. Polym.*, 5:310-326, 1990.
Dumitriu and Dumitriu, *Biomaterials*, 12:821-826, 1991.
Dumitriu et al., *Colloid. Polym. J.*, 269:1140-1147, 1991.
Dumitriu et al., *J. Biomat. Applications*, 6:80-88, 1991.
Dumitriu et al., In: *High Performance Biomaterials. A Comprehensive Guide to Medical and Pharmaceutical Applications*, Szycher (Ed.), Technomic Publ. Co., Inc., PA, 669-731, 1991.
Dumitriu et al., In: *Polymers in Medicine: Biomedical and Pharmaceutical Applications*, Ottenbritte and Chiellini (Eds.), Technomic Publ. Co., Inc., PA, 115-145, 1991.
Dumitriu et al., *Il Farmaco*, 47:509-518, 1992.
Dumitriu et al., *J. Biomat. Applications*, 6:251-260, 1992.
Dumitriu et al., *J. Biomat. Applications*, 7:265-276, 1993.
Elpern et al., *J. Crit. Illn.*, 9(12):1105-1110, 1994.
Gallivan, *Chest*, 119:1624-1625, 2001.
Groeger et al., *Ann. Surg.*, 218:106-10, 1993.
Heffner et al., *Chest*, 105(6):1743-1747, 1994.
Hentschel and Munstedt, *Infection*, 1:S43-45, 1999.
Herrington et al., *Pharmacotherapy*, 16(2):280-285, 1996.
Kennedy et al., *Chest*, 106(2):342-346, 1994.
Lee et al., *Respirology*, 7(3):209-16, 2002.
Lee et al., *Thorax*, 55(12):1058-62, 2000.
Li et al., *J. Biomater. Appl.*, 13:206-223, 1999.
Light et al., *Am. J. Respir. Crit. Care Med.*, 162(1):98-104, 2000.
Light et al., *Chest*, 106(2):577-582, 1994.
Light et al., *Chest*, 107(6):1702-1706, 1995.
Light et al., *JAMA*, 264(17):2224-2230, 1990.
Maki et al., *Am. J. Med.*, 85:307-14, 1988.
Maki et al., *Ann. Intern. Med.*, 127:257-266, 1997.
Mansson, *Scand. J. Infect. Dis. Suppl.*, 53:29-34, 1988.
Marchi et al., *Chest*, 128:1798-1804, 2005.
Marom et al., *Radiology*, 210(1):277-281, 1999.
Montes et al., *Am. J. Respir. Crit. Care Med.*, 168(3):348-355, 2003.
Paschoalini et al., *Chest*, 128(2):684-689, 2005.
Pulsiripunya et al., *Respirology*, 1(1):69-72, 1996.
Raad et al., *Biomaterials*, 17:1055-1059, 1996.
Raad et al., *J. Infect. Diseases*, 173:495-8, 1996.
Rinaldo et al., *J. Thorac. Cardiovas. Surg.*, 85(4):523-526, 1983.
Samuuel and Guggenbichler, *Int. J. Antimicrob. Agents*, 23S1:S75-S78, 2004.
Schaeffer et al., *J. Urol.*, 139:69-73, 1988.
Sherman et al., *Chest*, 93(3):533-536, 1988.
Sioshansi and Tobin, *Med. Plastics Biomat.*, 2:50-59, 1995.
Sioshansi, *Artif. Organs*, 18:266-271, 1994.
Sioshansi, *Orthopaedics Today*, 11:24-25, 1991.
Spadaro et al., *Agents Chemother.*, 6:637-642, 1974.
Stefani et al., *Eur. J. Cardiothorac. Surg.*, 30(6):827-832, 2006.
Thompson et al., *Ann. Pharmacother.*, 32(7-8):739-742, 1998.
Tobin and Bambauer, *Therap. Apheresis Dialysis*, 7(6):504-509, 2003.
Tremblay and Michaud, *Chest*, 129(2):362-368, 2006.
Vargas et al., *Chest*, 108(4):1080-1083, 1995.

Vargas et al., *Chest*, 118:808-813, 2000.
Wied et al., *J. Thorac. Cardiovasc. Surg.*, 1983; 86(4):591-593, 1983.
Wied et al., *Scand. J. Thorac. Cardiovasc. Surg.*, 15(3):305-307, 1981.

The invention claimed is:

1. A method of fusing two pleural layers, the method comprising:
   (a) providing a catheter coated with a sclerosing agent, wherein the catheter comprises a proximal end and a distal end, and wherein said catheter provides sustained release of the sclerosing agent into the pleural layer over a period of time greater than or equal to twenty-four hours; and
   (b) inserting the distal end of the catheter into a pleural space between a first pleural layer and a second pleural layer such that the catheter terminates in the pleural space, wherein the distal end of the catheter is inserted in an insertion point;
   wherein release of the sclerosing agent creates a diffuse pleurodesis of the first pleural layer and the second pleural layer, wherein:
      (i) the pleurodesis comprises a plurality of adhesions between the first pleural layer and the second layer;
      (ii) the plurality of adhesions cover at least twenty-five percent of the surface area of the first pleural layer; and
      (iii) at least one of the adhesions is more than five centimeters from the insertion point.

2. The method of claim 1, further comprising:
   providing a device that creates a negative pressure;
   coupling the device to the proximal end of the catheter; and
   operating the device provide a negative pressure to the pleural space.

3. The method of claim 2, wherein said device is a vacuum pump or vacuum compressor.

4. The method of claim 1, wherein the sustained release of the sclerosing agent into the pleural layer occurs over a time period of at least thirty-six hours.

5. The method of claim 1, wherein the sustained release of the sclerosing agent into the pleural layer occurs over a time period of at least forty-eight hours.

6. The method of claim 1, wherein the sustained release of the sclerosing agent into the pleural layer occurs over a time period of at least seventy-two hours.

7. The method of claim 1, further comprising draining a pleural effusion or air from the pleural space via the catheter.

8. The method of claim 7, wherein the pleural effusion is associated with cancer, congestive heart failure, cirrhosis, tuberculosis, pneumonia, pulmonary emboli, pancreatitis, or collagen vascular disease.

9. The method of claim 7, wherein the pleural effusion comprises a malignant pleural effusion.

10. The method of claim 7, further comprising:
    providing a device that creates a negative pressure;
    coupling the device to the catheter; and
    operating the device to provide a negative pressure to the pleural space.

11. The method of claim 9, further comprising draining the pleural effusion into a container coupled to the device.

12. The method of claim 1, wherein the sclerosing agent is a silver salt or a silver halide.

13. The method of claim 1, wherein the sclerosing agent is silver oxide, silver sulfate, silver carbonate, silver phosphate, silver sulfide, silver iodate, or silver sulphadiazine.

14. The method of claim 1, wherein the sclerosing agent is an antibiotic.

15. The method of claim 1, wherein the sclerosing agent is an antineoplastic agent.

16. The method of claim 1, wherein the sclerosing agent is a biological agent.

17. The method of claim 1, wherein the sclerosing agent is a cytokine.

18. The method of claim 1, wherein the sclerosing agent is doxycycline, minocycline, tetracycline, talc, bleomycin, doxorubicin, proviodine, TGF-β or mepacrine.

19. The method of claim 1, wherein the sclerosing agent is coated onto the catheter by spin coating, spraying, dipping or surface impregnating.

20. The method of claim 19, wherein the sclerosing agent in coated onto the catheter in a hydrogel.

* * * * *